(12) United States Patent
Wang et al.

(10) Patent No.: US 8,114,989 B2
(45) Date of Patent: *Feb. 14, 2012

(54) PYRAZOLYLAMINOPYRIMIDINE DERIVATIVES USEFUL AS TYROSINE KINASE INHIBITORS

(75) Inventors: Bin Wang, Longmont, CO (US); Tao Wang, Sudbury, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/713,777

(22) Filed: Feb. 26, 2010

(65) Prior Publication Data

US 2010/0210648 A1 Aug. 19, 2010

Related U.S. Application Data

(63) Continuation of application No. 11/914,492, filed as application No. PCT/GB2006/001760 on May 12, 2006, now abandoned.

(60) Provisional application No. 60/681,515, filed on May 16, 2005, provisional application No. 60/722,282, filed on Sep. 30, 2005.

(51) Int. Cl.
C07D 401/04 (2006.01)

(52) U.S. Cl. .................. 544/122; 544/234; 514/235.8; 514/275

(58) Field of Classification Search .............. 544/122, 544/234; 514/235.8, 275
See application file for complete search history.

(56) References Cited

U.S. PATENT DOCUMENTS

| | | | |
|---|---|---|---|
| 3,897,443 A | 7/1975 | Sharpe | |
| 4,038,240 A | 7/1977 | Hugl et al. | |
| 4,485,284 A | 11/1984 | Pakulis | |
| 5,147,876 A | 9/1992 | Mizuchi et al. | |
| 5,459,318 A | 10/1995 | Cacho et al. | |
| 5,521,184 A | 5/1996 | Zimmermann | |
| 6,383,553 B1 | 5/2002 | Tondar et al. | |
| 6,399,780 B1 | 6/2002 | Hudkins | |
| 6,455,525 B1 | 9/2002 | Singh et al. | |
| 6,610,677 B2 | 8/2003 | Davies et al. | |
| 6,613,776 B2 | 9/2003 | Knegtel et al. | |
| 6,638,926 B2 | 10/2003 | Davies et al. | |
| 6,653,300 B2 | 11/2003 | Bebbington et al. | |
| 6,653,301 B2 | 11/2003 | Bebbington et al. | |
| 6,656,939 B2 | 12/2003 | Bebbington et al. | |
| 6,660,731 B2 | 12/2003 | Bebbington et al. | |
| 6,664,247 B2 | 12/2003 | Bebbington et al. | |
| 6,696,452 B2 | 2/2004 | Davies et al. | |
| 6,727,251 B2 | 4/2004 | Bebbington et al. | |
| 6,989,385 B2 | 1/2006 | Bebbington et al. | |
| 7,008,948 B2 | 3/2006 | Bebbington et al. | |
| 7,087,603 B2 | 8/2006 | Bebbington et al. | |
| 7,098,330 B2 | 8/2006 | Bebbington et al. | |
| 7,115,739 B2 | 10/2006 | Bebbington et al. | |
| 7,148,455 B2 | 12/2006 | Scalese et al. | |
| 7,183,307 B2 | 2/2007 | Hale et al. | |
| 7,279,476 B2 | 10/2007 | Tang et al. | |
| 7,390,815 B2 | 6/2008 | Davies et al. | |
| 7,427,681 B2 | 9/2008 | Bebbington et al. | |
| 7,473,691 B2 | 1/2009 | Davies et al. | |
| 7,521,453 B2 * | 4/2009 | Barlaam et al. | 514/255.05 |
| 7,528,138 B2 | 5/2009 | Knegtel et al. | |
| 7,528,142 B2 | 5/2009 | Binch et al. | |
| 7,531,536 B2 | 5/2009 | Bebbington et al. | |
| 2003/0055068 A1 | 3/2003 | Bebbington et al. | |
| 2003/0078275 A1 | 4/2003 | Bebbington et al. | |
| 2003/0079365 A1 | 5/2003 | Corak et al. | |
| 2003/0105090 A1 | 6/2003 | Bebbington et al. | |
| 2005/0038023 A1 | 2/2005 | Bebbington et al. | |
| 2005/0054638 A1 | 3/2005 | Barlaam et al. | |
| 2007/0142413 A1 | 6/2007 | Block et al. | |
| 2008/0004302 A1 | 1/2008 | Theoclitou et al. | |
| 2008/0108633 A1 | 5/2008 | Claesson | |
| 2008/0108669 A1 | 5/2008 | Claesson | |

(Continued)

FOREIGN PATENT DOCUMENTS

EP 0401358 12/1990

(Continued)

OTHER PUBLICATIONS

Aimone et al. "Antinociceptive Activity of Selective Tyrosine Kinase Inhibitors in the Rat". Abstracts of the Annual Meeting of the Society for Neuroscience (2000), vol. 26, No. 1-2, 1692, XP008129558.

Alferez et al. "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Abstract 471.

Alferez et al. "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Poster.

(Continued)

Primary Examiner — Deepak Rao

(57) ABSTRACT

This invention relates to novel compounds having the formula (I):

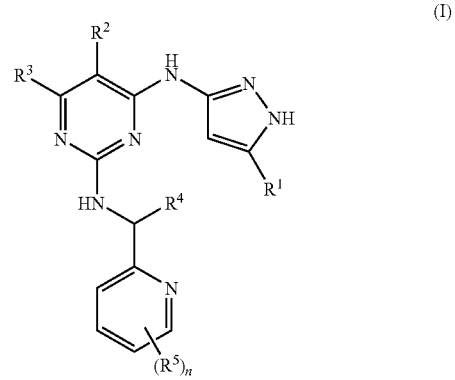

and to their pharmaceutical compositions and to their methods of use. These novel compounds provide a treatment for cancer.

1 Claim, No Drawings

U.S. PATENT DOCUMENTS

| | | | | |
|---|---|---|---|---|
| 2008/0139561 A1* | 6/2008 | Davies et al. | ............... | 514/236.5 |
| 2008/0176872 A1 | 7/2008 | Lamb et al. | | |
| 2008/0194606 A1 | 8/2008 | Scott et al. | | |
| 2008/0287437 A1 | 11/2008 | Wang et al. | | |
| 2008/0287475 A1 | 11/2008 | Feng et al. | | |
| 2009/0005396 A1 | 1/2009 | Claesson | | |
| 2010/0152219 A1 | 6/2010 | Block et al. | | |

FOREIGN PATENT DOCUMENTS

| | | |
|---|---|---|
| EP | 1317448 | 5/2005 |
| EP | 1317444 | 5/2006 |
| EP | 1317447 | 5/2006 |
| EP | 1317449 | 5/2006 |
| EP | 1317452 | 5/2006 |
| EP | 1318997 | 5/2006 |
| EP | 1345922 | 5/2006 |
| EP | 1345926 | 5/2006 |
| EP | 1345927 | 5/2006 |
| EP | 1345929 | 5/2006 |
| EP | 1353916 | 9/2006 |
| EP | 1345928 | 2/2007 |
| EP | 1876178 | 1/2008 |
| EP | 1686999 | 7/2009 |
| WO | WO 95/09852 | 4/1995 |
| WO | WO 97/09325 | 3/1997 |
| WO | WO 97/19065 | 5/1997 |
| WO | WO 98/38171 | 9/1998 |
| WO | WO 99/41253 | 8/1999 |
| WO | WO 00/12485 | 3/2000 |
| WO | WO 00/14552 | 3/2000 |
| WO | WO 00/16067 | 3/2000 |
| WO | WO 00/27825 | 5/2000 |
| WO | WO 00/35455 | 6/2000 |
| WO | WO 00/39101 | 7/2000 |
| WO | WO 00/53595 | 9/2000 |
| WO | WO 00/63182 | 10/2000 |
| WO | WO 00/73344 | 12/2000 |
| WO | WO 00/78731 | 12/2000 |
| WO | WO 01/17995 | 3/2001 |
| WO | WO 01/22938 | 4/2001 |
| WO | WO 01/47921 | 7/2001 |
| WO | WO 01/60816 | 8/2001 |
| WO | WO 01/64655 | 9/2001 |
| WO | WO 01/64656 | 9/2001 |
| WO | WO 01/85699 | 11/2001 |
| WO | WO 02/18346 | 3/2002 |
| WO | WO 02/20479 | 3/2002 |
| WO | WO 02/20513 | 3/2002 |
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | WO 02/50065 | 6/2002 |
| WO | WO 02/50066 | 6/2002 |
| WO | WO 02/50071 | 6/2002 |
| WO | WO 02/059111 | 8/2002 |
| WO | WO 02/064096 | 8/2002 |
| WO | WO 03/026665 | 4/2003 |
| WO | WO 03/027111 | 4/2003 |
| WO | WO 03/048133 * | 6/2003 |
| WO | WO 2004/037814 | 5/2004 |
| WO | WO 2005/016893 | 2/2005 |
| WO | WO 2005/048133 | 5/2005 |
| WO | WO 2005/049033 | 6/2005 |
| WO | WO 2005/095400 | 10/2005 |
| WO | WO 2005/103010 | 11/2005 |
| WO | WO 2006/037117 | 4/2006 |
| WO | WO 2006/048080 | 5/2006 |
| WO | WO 2006/067614 | 6/2006 |
| WO | WO 2006/074057 | 7/2006 |
| WO | WO 2006/082392 | 8/2006 |
| WO | WO 2006/087530 | 8/2006 |
| WO | WO 2006/087538 | 8/2006 |
| WO | WO 2006/115452 | 11/2006 |
| WO | WO 2006/123113 | 11/2006 |
| WO | WO 2007/049041 | 5/2007 |
| WO | WO 2007/071348 | 6/2007 |
| WO | WO 2008/005538 | 1/2008 |
| WO | WO 2008/135785 | 11/2008 |
| WO | WO 2010/038060 | 4/2010 |

OTHER PUBLICATIONS

Blowers "AZD8931". IASLC Annual Targeted Therapies of the Treatment of Lung Cancer Meeting (2011), Santa Monica, CA, PowerPoint Presentation.

Breault et al. "Cyclin-Dependent Kinase 4 Inhibitors as a Treatment for Cancer. Part 2: Identification and Optimisation of Substituted 2, 4-Bis Anilino Pyrimidines". Bioorganic & Medicinal Chemistry Letters (2003), vol. 13, 2961-2966.

Cristofanilli et al. "Exploratory Subset Analysis According to Prior Endocrine Treatment of Two Randomized Phase II Trials Comparing Gefitinib (G) with Placebo (P) in Combination with Tamoxifen (T) or Anastrozole (A) in Hormone Receptor-Positive (HR+) Metastatic Breast Cancer (MBC)". J Clin. Oncol. (2009), vol. 27, 15s, Abstract 1014.

El Kerdaway et al. "2, 4-Bis (substituted)-5-nitropyrimidines of Expected Diuretic Action". Egypt J. Chem (1986), vol. 92, No. 2, 247-251.

Hefti et al. "Novel Class of Pain Drugs Based on Antagonism of NGF". Trends in Pharmacological Sciences (2006), vol. 27, No. 2, 85-91.

Hickinson et al. "AZD8931, an Equipotent, Reversible Inhibitor of Signaling by Epidermal Growht Factor Receptor, ERBB2 (HER2), and ERBB3: A Unique Agent for Simultaneous ERBB Receptor Blockage in Cancer". Clinical Cancer Research (2010) vol. 16, 1159-1169.

International Search Report for corresponding PCT application No. PCT/GB2006/000334 (2006).

Keilholz et al. "Phase I Dose-Finding Study of Monotherapy with AZD8931, an Inhibitor of erbB1, 2 and 3 Signaling, in Patients with Advanced Solid Tumors". J Clin Oncol. (2011), vol. 29, Abstract 3097.

Keilholz et al. "Phase I Dose-Finding Study of Monotherapy with AZD8931, an Inhibitor of erbB1, 2 and 3 Signaling, in Patients with Advanced Solid Tumors". ASCO (2011), Poster.

Klinowska et al. "AZD8931, an Equipotent, Reversible Inhibitor of erbB1, erbB2 and erbB3 Receptor Signaling: Characterisation of Pharmacological Profile". European Journal of Cancer Supplements (2009), vol. 7, No. 2, 127.

Leroith and Roberts. "The Insulin-Like Growth Factor System and Cancer". Cancer Letters (2003), vol. 195, 127-137.

Lopez-Martin et al. "Phase I Dose-Finding Study of AZD8931, an Inhibitor of erbB1, 2 and 3 Receptor Signaling, in Combination with Paclitaxel". J Clin. Oncol. (2011), vol. 29, Abstract 3105.

Lopez-Martin et al. "Phase I Dose-Finding Study of AZD8931, an Inhibitor of erbB1, 2 and 3 Receptor Signaling, in Combination with Paclitaxel". ASCO (2011), Poster.

Marshall et al. "Evaluation of AZD8931, an Equipotent Inhibitor of erbB 1, erbB2 and erbB3 Receptor Signaling, on Ligand Stimulated Breast Cancer Cell Lines with Differing Levels of erbB2 Expression". SABCS (2009), Abstract 5059.

Normanno et al. "Target-based therapies in breast cancer: current status and future perspectives". Endocr Relat Cancer (2009), vol. 16(3): 675-702.

Parrizas et al. "Specific Inhibition of Insulin-Like Growth Factor-1 and Insulin Receptor Tyrosine Kinase Activity and Biological Function by Tyrphostins". Endocrinology (1997), vol. 138, No. 4, 1427-1433.

Pierce et al. "CH . . .O and CH . . . N Hydrogen Bonds in Ligand Design: A Novel Quinazolin-4-ylthiazol-2-ylamine Protein Kinase Inhibitor". J. Med. Chem. (2005), vol. 48, 1278-1281.

Simone "Oncology: Introduction, Cecil Textbook of Medicine, 20TH Edition" (1996), vol. 1, 1004-1010.

Speake et al. "Characterization of AZD8931, a Potent Reversible Small Molecule Inhibitor Against Epidermal Growth Factor Receptor (EGFR), Erythroblastic Leukemia Viral Oncogene Homolog 2 (HER2) and 3 (HER3) with a Unique and Balanced Pharmacological Profile". J Clin. Oncol. (2009), vol. 27, 15s, Abstract 11072.

Thress et al. "Identification and Preclinical Characterization of AZ-23, a Novel, Selective, and Orally Bioavailable Inhibitor of the Trk Kinase Pathway". Molecular Cancer Therapeutics (2009) vol. 8, No. 7, 1818-1827.

Ulrich et al. "Chapter 4: Crystallization". Kirk-Othmer Encyclopedia of Chemical Technology (Aug. 2002).

Vippagunta et al. "Crystalline Solids". Advanced Drug Delivery Reviews (2001), vol. 48, 3-26.

Wang et al. "Identification of 4-Aminopyrazolylpyrimidines as Potent Inhibitors of Trk Kinases". J. Med. Chem. (2008), vol. 51, No. 15, 4672-4684, ACS Publications, DC, US.

Wang et al. "Trik Kinase Inhibitors as New Treatments for Cancer and Pain". Expert Opin. Ther. Patents (2009), vol. 19, No. 3, 305-319.

West "Chapter 10: Solid Solutions". Solid State Chemistry and Its Applications (1988), 358 & 365.

Winston et al. "Suppression of Neuronal Tyrosine Kinase Activity in Associated with Improvement in Pain Responses and Inhibition of Nociceptive Gene Expression in Pancreatitis". Abstracts of the Annual Meeting of the Society for Neuroscience (2001), vol. 27, 2162, XP008129567.

* cited by examiner

PYRAZOLYLAMINOPYRIMIDINE DERIVATIVES USEFUL AS TYROSINE KINASE INHIBITORS

This application is a continuation of Ser. No. 11/914,492 filed Nov. 15, 2007 now abandoned, which is a 371 of PCT/GB06/01760 filed May 12, 2006 which claims benefit of U.S. Provisional Application No. 60/681,515 filed May 16, 2005 and U.S. Provisional Application No. 60/722,282 filed Sep. 30, 2005.

FIELD OF THE INVENTION

The present invention relates to novel pyrazole derivatives, their pharmaceutical compositions and methods of use. In addition, the present invention relates to therapeutic methods for the treatment and prevention of cancers and to the use of these pyrazole derivatives in the manufacture of medicaments for use in the treatment and prevention of cancers.

BACKGROUND OF THE INVENTION

Receptor tyrosine kinases (RTK's) are a sub-family of protein kinases that play a critical role in cell signalling and are involved in a variety of cancer related processes including cell proliferation, survival, angiogenesis and metastasis. Currently up to 100 different RTK's including tropomyosin-related kinases (Trk's) have been identified.

Trk's are the high affinity receptors activated by a group of soluble growth factors called neurotrophins (NT). The Trk receptor family has three members—TrkA, TrkB and TrkC. Among the NTs there are (i) nerve growth factor (NGF) which activates TrkA, (ii) brain-derived growth factor (BDNF) and NT-4/5 which activate TrkB and (iii) NT3 which activates TrkC. Each Trk receptor contains an extra-cellular domain (ligand binding), a trans-membrane region and an intra-cellular domain (including kinase domain). Upon binding of the ligand, the kinase catalyzes auto-phosphorylation and triggers downstream signal transduction pathways.

Trk's are widely expressed in neuronal tissue during its development where Trk's are critical for the maintenance and survival of these cells. A post-embryonic role for the Trk/neurotrophin axis (or pathway), however, remains in question. There are reports showing that Trk's play important role in both development and function of the nervous system (Patapoutian, A. et al *Current Opinion in Neurobiology*, 2001, 11, 272-280).

In the past decade, a considerable number of literature documentations linking Trk signalling with cancer have published. For example, while Trk's are expressed at low levels outside the nervous system in the adult, Trk expression is increased in late stage prostate cancers. Both normal prostate tissue and androgen-dependent prostate tumours express low levels of Trk A and undetectable levels of Trk B and C. However, all isoforms of Trk receptors as well as their cognate ligands are up-regulated in late stage, androgen-independent prostate cancer. There is additional evidence that these late stage prostate cancer cells become dependent on the Trk/neurotrophin axis for their survival. Therefore, Trk inhibitors may yield a class of apoptosis-inducing agents specific for androgen-independent prostate cancer (Weeraratna, A. T. et al *The Prostate*, 2000, 45, 140-148).

Furthermore, very recent literature also shows that overexpression, activation, amplification and/or mutation of Trk's are associated with secretory breast carcinoma (*Cancer Cell*, 2002, 2, 367-376), colorectal cancer (Bardelli et al *Science*, 2003, 300, 949-949) and ovarian cancer (Davidson, B. et al *Clinical Cancer Research*, 2003, 9, 2248-2259).

There are a few reports of selective Trk tyrosine kinase inhibitors. Cephalon described CEP-751, CEP-701 (George, D. et al *Cancer Research*, 1999, 59, 2395-2341) and other indolocarbazole analogues (WO0114380) as Trk inhibitors. It was shown that CEP-701 and/or CEP751, when combined with surgically or chemically induced androgen ablation, offered better efficacy compared with mono-therapy alone. GlaxoSmithKline disclosed certain oxindole compounds as Trk A inhibitors in WO0220479 and WO0220513. Recently, Japan Tobacco reported pyrazolyl condensed cyclic compounds as Trk inhibitors (JP2003231687A).

In addition to the above, Vertex Pharmaceuticals have described pyrazole compounds as inhibitors of GSK3, Aurora, etc. in WO0250065, WO0262789, WO03027111 and WO200437814; and AstraZeneca have reported pyrazole compounds as inhibitors against IGF-1 receptor kinase (WO0348133). AstraZeneca have also reported Trk inhibitors in International Applications WO 2005/049033 and WO 2005/103010.

SUMMARY OF THE INVENTION

In accordance with the present invention, the applicants have hereby discovered novel pyrazole compounds, or pharmaceutically acceptable salts thereof, which possess Trk kinase inhibitory activity and are accordingly useful for their anti-proliferation and/or proapoptotic (such as anti-cancer) activity and in methods of treatment of the human or animal body. The invention also relates to processes for the manufacture of said pyrazole compounds, or pharmaceutically acceptable salts thereof, to pharmaceutical compositions containing them and to their use in the manufacture of medicaments for use in the production of an anti-proliferation and/or proapoptotic effect in warm-blooded animals such as man.

Also in accordance with the present invention the applicants provide methods of using such pyrazole compounds, or pharmaceutically acceptable salts thereof, in the treatment of cancer.

The properties of the compounds claimed in this invention are expected to be of value in the treatment of disease states associated with cell proliferation such as cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Furthermore, the compounds, or pharmaceutically acceptable salts thereof, of the invention are expected to be of value in the treatment or prophylaxis of cancers selected from congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposi sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma and leukaemia; particularly ovarian cancer, breast cancer, colorectal cancer, prostate cancer and lung cancer—NSCLC and SCLC; more particularly prostate cancer; and more particularly hormone refractory prostate cancer.

DETAILED DESCRIPTION OF THE INVENTION

Accordingly, the present invention provides a compound of formula (I):

(I)

wherein:
$R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$-amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{19}$— or heterocyclyl-$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$carbamoyl, $C_{1-6}$alkoxycarbonyl, carbocyclyl or heterocyclyl; wherein $R^4$ may be optionally substituted on carbon by one or more $R^{19}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by one or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from a direct bond, —O—, —N($R^{22}$)—, —C(O)—, —N($R^{23}$)C(O)—, —C(O)N ($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

According to a further aspect of the present invention there is provided a compound of formula (I) wherein:

$R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$-amino, $C_{1-6}$alkanoylamino, $C_{1-6}$alkylsulphonylamino, 3-5- membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$-carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

According to a further feature of the present invention there is provided a compound of formula (I) wherein:

$R^1$ is selected from hydrogen, hydroxy, amino, mercapto, $C_{1-6}$alkyl, $C_{2-6}$alkenyl, $C_{2-6}$alkynyl, $C_{1-6}$alkoxy, $C_{1-6}$alkanoyloxy, N—($C_{1-6}$alkyl)amino, N,N—($C_{1-6}$alkyl)$_2$-amino, $C_{1-6}$alkanoylamino, $C_{1-6}$alkylsulphonylamino, 3-5-membered carbocyclyl or 3-5-membered heterocyclyl; wherein $R^1$ may be optionally substituted on carbon by one or more $R^6$; and wherein if said heterocyclyl contains an —NH— moiety that nitrogen may be optionally substituted by a group selected from $R^7$;

$R^2$ and $R^3$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{19}$— or heterocyclyl—$R^{21}$—; wherein $R^2$ and $R^3$ independently of each other may be optionally substituted on carbon by one or more $R^8$; and wherein if said heterocyclyl contains an —NH— moiety that nitrogen may be optionally substituted by a group selected from $R^9$;

$R^4$ is selected from cyano, carboxy, carbamoyl, $C_{1-6}$alkyl, $C_{2-6}$alkenyl, $C_{2-6}$alkynyl, $C_{1-6}$alkanoyl, N—($C_{1-6}$alkyl)carbamoyl, N,N—($C_{1-6}$alkyl)$_2$-carbamoyl, $C_{1-6}$alkoxycarbonyl, carbocyclyl or heterocyclyl; wherein $R^4$ may be optionally substituted on carbon by one or more $R^{10}$; and wherein if said heterocyclyl contains an —NH— moiety that nitrogen may be optionally substituted by a group selected from $R^{11}$;

$R^5$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{12}$; and wherein if said heterocyclyl contains an —NH— moiety that nitrogen may be optionally substituted by a group selected from $R^{13}$;

n=1, 2 or 3; wherein the values of $R^5$ may be the same or different;

$R^6$, $R^8$, $R^{10}$ and $R^{12}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$ alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^6$, $R^8$, $R^{10}$ and $R^{12}$ independently of each other may be optionally substituted on carbon by one or more $R^{14}$; and wherein if said heterocyclyl contains an —NH— moiety that nitrogen may be optionally substituted by a group selected from $R^{15}$;

$R^7$, $R^9$, $R^{11}$, $R^{13}$ and $R^{15}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^9$, $R^{11}$, $R^{13}$ and $R^{15}$ independently of each other may be optionally substituted on carbon by on or more $R^{16}$;

$R^{14}$ and $R^{16}$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS (O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{14}$ and $R^{16}$ independently of each other may be optionally substituted on carbon by one or more $R^{17}$; and wherein if said heterocyclyl contains an —NH— moiety that nitrogen may be optionally substituted by a group selected from $R^{18}$;

$R^{17}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{19}$ and $R^{21}$ are independently selected from —O—, —N($R^{22}$)—, —C(O)—, —N($R^{23}$)C(O)—, —C(O)N($R^{24}$)—, —S(O)$_s$—, —SO$_2$N($R^{25}$)— or —N($R^{26}$)SO$_2$—; wherein $R^{22}$, $R^{23}$, $R^{24}$, $R^{25}$ and $R^{26}$ are independently selected from hydrogen or $C_{1-6}$alkyl and s is 0-2;

$R^{18}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

Particular values of the variable groups contained in formula (I) are as follows. Such values may be used, where appropriate, with any of the definitions, claims or embodiments defined hereinbefore or hereinafter.

$R^1$ is selected from $C_{1-6}$alkyl, $C_{1-6}$alkoxy or 3-5-membered carbocyclyl.

$R^1$ is selected from $C_{1-6}$alkoxy or 3-5-membered carbocyclyl.

$R^1$ is 3-5-membered carbocyclyl.

$R^1$ is selected from $C_{1-6}$alkyl, $C_{1-6}$alkoxy or 3-membered carbocyclyl.

$R^1$ is selected from $C_{1-6}$alkoxy or 3-membered carbocyclyl.

$R^1$ is 3-membered carbocyclyl.

$R^1$ is selected from methyl, methoxy, isopropoxy or cyclopropyl.

$R^1$ is selected from isopropoxy or cyclopropyl.

$R^1$ is selected from methyl.

$R^1$ is selected from methoxy.

$R^1$ is cyclopropyl.

$R^1$ is isopropoxy.

$R^2$ is selected from hydrogen and halo.

$R^2$ is selected from hydrogen, fluoro, chloro and bromo.

$R^2$ is chloro.

$R^2$ is hydrogen.

$R^3$ is selected from hydrogen, halo, amino, $C_{1-6}$alkoxy, N—($C_{1-6}$alkyl)amino or heterocyclyl-$R^{21}$—; wherein $R^3$ may be optionally substituted on carbon by one or more $R^8$; wherein $R^8$ is selected from hydroxy, carbocyclyl or heterocyclyl; wherein $R^8$ may be optionally substituted on carbon by one or more $R^{14}$;

$R^{14}$ is $C_{1-6}$alkyl;

$R^{21}$ is a direct bond or —O—.

$R^3$ is selected from hydrogen, halo, amino, $C_{1-6}$alkoxy, N—($C_{1-6}$alkyl)amino or heterocyclyl-$R^{21}$—; wherein $R^3$ may be optionally substituted on carbon by one or more $R^8$; wherein $R^8$ is selected from hydroxy, carbocyclyl or heterocyclyl; wherein $R^8$ may be optionally substituted on carbon by one or more $R^{14}$;

$R^{14}$ is $C_{1-6}$alkyl;

$R^{21}$ is —O—.

$R^3$ is selected from hydrogen, chloro, amino, methoxy, propoxy, isopropoxy, propylamino, isopropylamino, morpholino-$R^{21}$— and 1,3-dioxan-5-yl-$R^{21}$—; wherein $R^3$ may be optionally substituted on carbon by one or more $R^8$; wherein $R^8$ is selected from hydroxy, phenyl or 1,3-dioxolan-4-yl; wherein $R^8$ may be optionally substituted on carbon by one or more $R^{14}$;

$R^{14}$ is methyl;

$R^{21}$ is a direct bond or —O—.

$R^3$ is selected from hydrogen, chloro, amino, methoxy, propoxy, isopropoxy, propylamino, isopropylamino and 1,3-dioxan-5-yl-$R^{21}$—; wherein $R^3$ may be optionally substituted on carbon by one or more $R^8$; wherein $R^8$ is selected from hydroxy, phenyl or 1,3-dioxolan-4-yl; wherein $R^8$ may be optionally substituted on carbon by one or more $R^{14}$;

$R^{14}$ is methyl;

$R^{21}$ is —O—.

$R^3$ is selected from hydrogen, chloro, amino, 2,3-dihydroxypropoxy, 1,3-dihydroxyprop-2-yloxy, 2,3-dihydroxypropylamino, 1,3-dihydroxyprop-2-ylamino, 2,2-dimethyl-1,3,-dioxolan-4-ylmethoxy, morpholino and 2-phenyl-1,3-dioxan-5-yloxy.

$R^3$ is selected from hydrogen, chloro, amino, 2,3-dihydroxypropoxy, 1,3-dihydroxyprop-2-yloxy, 2,3-dihydroxypropylamino, 1,3-dihydroxyprop-2-ylamino, 2,2-dimethyl-1,3,-dioxolan-4-ylmethoxy and 2-phenyl-1,3-dioxan-5-yloxy.

$R^3$ is selected from hydrogen, chloro, amino, 2,3-dihydroxypropoxy, 1,3-dihydroxyprop-2-yloxy, 2,3-dihydroxypropylamino, 1,3-dihydroxyprop-2-ylamino, (R)-2,2-dimethyl-1,3,-dioxolan-4-ylmethoxy, morpholino and (cis)-2-phenyl-1,3-dioxan-5-yloxy.

$R^3$ is selected from hydrogen, chloro, amino, 2,3-dihydroxypropoxy, 1,3-dihydroxyprop-2-yloxy, 2,3-dihydroxypropylamino, 1,3-dihydroxyprop-2-ylamino, (R)-2,2-dimethyl-1,3,-dioxolan-4-ylmethoxy and (cis)-2-phenyl-1,3-dioxan-5-yloxy.

$R^3$ is selected from halo.

$R^3$ is selected from hydrogen.

$R^3$ is selected from fluoro, chloro or bromo.

$R^2$ and $R^3$ are independently selected from hydrogen, halo, amino, $C_{1-6}$alkoxy, N—($C_{1-6}$alkyl)amino or heterocyclyl-$R^{21}$—; wherein $R^2$ or $R^3$ may be optionally substituted on carbon by one or more $R^8$; wherein $R^8$ is selected from hydroxy, carbocyclyl or heterocyclyl; wherein $R^8$ may be optionally substituted on carbon by one or more $R^{14}$;

$R^{14}$ is $C_{1-6}$alkyl;

$R^{21}$ is a direct bond or —O—.

$R^2$ and $R^3$ are independently selected from hydrogen, halo, amino, $C_{1-6}$alkoxy, N—($C_{1-6}$alkyl)amino or heterocyclyl-$R^{21}$—; wherein $R^3$ may be optionally substituted on carbon by one or more $R^8$; wherein $R^8$ is selected from hydroxy, carbocyclyl or heterocyclyl; wherein $R^8$ may be optionally substituted on carbon by one or more $R^{14}$;

$R^{14}$ is $C_{1-6}$alkyl;

$R^{21}$ is —O—.

$R^2$ and $R^3$ are independently selected from hydrogen or halo.

$R^2$ and $R^3$ are independently selected from hydrogen, fluoro, chloro, bromo, amino, methoxy, propoxy, isopropoxy, propylamino, isopropylamino, morpholino-$R^{21}$— and 1,3-dioxan-5-yl-$R^{21}$—; wherein $R^2$ or $R^3$ may be optionally substituted on carbon by one or more $R^8$; wherein $R^8$ is selected from hydroxy, phenyl or 1,3-dioxolan-4-yl; wherein $R^8$ may be optionally substituted on carbon by one or more $R^{14}$;

$R^{14}$ is methyl;

$R^{21}$ is a direct bond or —O—.

$R^2$ and $R^3$ are independently selected from hydrogen, fluoro, chloro, bromo, amino, methoxy, propoxy, isopropoxy, propylamino, isopropylamino and 1,3-dioxan-5-yl-$R^{21}$—; wherein $R^3$ may be optionally substituted on carbon by one or more $R^8$; wherein $R^8$ is selected from hydroxy, phenyl or 1,3-dioxolan-4-yl; wherein $R^8$ may be optionally substituted on carbon by one or more $R^{14}$;

$R^{14}$ is methyl;

$R^{21}$ is —O—.

$R^2$ and $R^3$ are independently selected from hydrogen, fluoro, chloro, bromo, amino, 2,3-dihydroxypropoxy, 1,3-dihydroxyprop-2-yloxy, 2,3-dihydroxypropylamino, 1,3-dihydroxyprop-2-ylamino, 2,2-dimethyl-1,3,-dioxolan-4-ylmethoxy, morpholino and 2-phenyl-1,3-dioxan-5-yloxy.

$R^2$ and $R^3$ are independently selected from hydrogen, fluoro, chloro, bromo, amino, 2,3-dihydroxypropoxy, 1,3-dihydroxyprop-2-yloxy, 2,3-dihydroxypropylamino, 1,3-dihydroxyprop-2-ylamino, 2,2-dimethyl-1,3,-dioxolan-4-ylmethoxy and 2-phenyl-1,3-dioxan-5-yloxy.

$R^2$ and $R^3$ are independently selected from hydrogen, fluoro, chloro, bromo, amino, (R)-2,3-dihydroxypropoxy, (S)-2,3-dihydroxypropoxy, 1,3-dihydroxyprop-2-yloxy, (R)-2,3-dihydroxypropylamino, 1,3-dihydroxyprop-2-ylamino, (R)-2,2-dimethyl-1,3,-dioxolan-4-ylmethoxy, morpholino and (cis)-2-phenyl-1,3-dioxan-5-yloxy.

$R^2$ and $R^3$ are independently selected from hydrogen, fluoro, chloro, bromo, amino, (R)-2,3-dihydroxypropoxy, (S)-2,3-dihydroxypropoxy, 1,3-dihydroxyprop-2-yloxy, (R)-2,3-dihydroxypropylamino, 1,3-dihydroxyprop-2-ylamino, (R)-2,2-dimethyl-1,3,-dioxolan-4-ylmethoxy and (cis)-2-phenyl-1,3-dioxan-5-yloxy.

$R^2$ and $R^3$ are independently selected from hydrogen, fluoro, chloro or bromo.

$R^4$ is selected from $C_{1-6}$alkyl.

$R^4$ is selected from methyl.

$R^4$ is selected from (S)-methyl.

$R^5$ is selected from halo, $C_{1-6}$alkyl or carbocyclyl.

$R^5$ is halo.

$R^5$ is selected from fluoro, bromo, methyl or cyclopropyl.

$R^5$ is fluoro.

$R^5$ is fluoro para to the —CH($R^4$)— group.

n is 1 or 2 and one $R^5$ is para to the —CH($R^4$)— group.

n is 1 and $R^5$ is para to the —CH($R^4$)— group.

n is 1 and $R^5$ is fluoro para to the —CH($R^4$)— group.

n=1.

n=1 or 2; wherein the values of $R^5$ may be the same or different.

n=2; wherein the values of $R^5$ may be the same or different.

n=3; wherein the values of $R^5$ may be the same or different.

Therefore in a further aspect of the invention there is provided a compound of formula (I) (as depicted herein above) wherein:

$R^1$ is selected from $C_{1-6}$alkyl, $C_{1-6}$alkoxy or 3-5-membered carbocyclyl;

$R^2$ is selected from hydrogen and halo;

$R^3$ is selected from hydrogen, halo, amino, $C_{1-6}$alkoxy, N—($C_{1-6}$alkyl)amino or heterocyclyl-$R^{21}$—; wherein $R^3$ may be optionally substituted on carbon by one or more $R^8$;

$R^4$ is selected from $C_{1-6}$alkyl;

$R^5$ is selected from halo, $C_{1-6}$alkyl or carbocyclyl;

n=1 or 2; wherein the values of $R^5$ may be the same or different;

$R^8$ is selected from hydroxy, carbocyclyl or heterocyclyl; wherein $R^8$ may be optionally substituted on carbon by one or more $R^{14}$;

$R^{14}$ is $C_{1-6}$alkyl;

$R^{21}$ is a direct bond or —O—;

or a pharmaceutically acceptable salt thereof.

Therefore in a further aspect of the invention there is provided a compound of formula (I) (as depicted herein above) wherein:

$R^1$ is selected from $C_{1-6}$alkoxy or 3-5-membered carbocyclyl;

$R^2$ is selected from hydrogen and halo;

$R^3$ is selected from hydrogen, halo, amino, $C_{1-6}$alkoxy, N—($C_{1-6}$alkyl)amino or heterocyclyl-$R^{21}$—; wherein $R^3$ may be optionally substituted on carbon by one or more $R^8$;

$R^4$ is selected from $C_{1-6}$alkyl;

$R^5$ is selected from halo, $C_{1-6}$alkyl or carbocyclyl;

n=1 or 2; wherein the values of $R^5$ may be the same or different;

$R^8$ is selected from hydroxy, carbocyclyl or heterocyclyl; wherein $R^8$ may be optionally substituted on carbon by one or more $R^{14}$;

$R^{14}$ is $C_{1-6}$alkyl;

$R^{21}$ is —O—;

or a pharmaceutically acceptable salt thereof.

Therefore in a further aspect of the invention there is provided a compound of formula (I) (as depicted herein above) wherein:

$R^1$ is 3-5-membered carbocyclyl;
$R^2$ and $R^3$ are independently selected from hydrogen or halo;
$R^4$ is selected from $C_{1-6}$alkyl;
$R^5$ is halo; and
n=1;
or a pharmaceutically acceptable salt thereof.

Therefore in a further aspect of the invention there is provided a compound of formula (I) (as depicted herein above) wherein:

$R^1$ is selected from methyl, methoxy, isopropoxy or cyclopropyl;
$R^2$ is selected from hydrogen, fluoro, chloro and bromo;
$R^3$ is selected from hydrogen, chloro, amino, 2,3-dihydroxypropoxy, 1,3-dihydroxyprop-2-yloxy, 2,3-dihydroxypropylamino, 1,3-dihydroxyprop-2-ylamino, 2,2-dimethyl-1,3,-dioxolan-4-ylmethoxy, morpholino and 2-phenyl-1,3-dioxan-5-yloxy;
$R^4$ is selected from methyl;
$R^5$ is selected from fluoro, bromo, methyl or cyclopropyl;
n=1 or 2; wherein the values of $R^5$ may be the same or different;
or a pharmaceutically acceptable salt thereof.

Therefore in a further aspect of the invention there is provided a compound of formula (I) (as depicted herein above) wherein:

$R^1$ is selected from isopropoxy or cyclopropyl;
$R^2$ is selected from hydrogen, fluoro, chloro and bromo;
$R^3$ is selected from hydrogen, chloro, amino, 2,3-dihydroxypropoxy, 1,3-dihydroxyprop-2-yloxy, 2,3-dihydroxypropylamino, 1,3-dihydroxyprop-2-ylamino, 2,2-dimethyl-1,3,-dioxolan-4-ylmethoxy and 2-phenyl-1,3-dioxan-5-yloxy;
$R^4$ is selected from methyl;
$R^5$ is selected from fluoro, bromo, methyl or cyclopropyl;
n=1 or 2; wherein the values of $R^5$ may be the same or different;
or a pharmaceutically acceptable salt thereof.

Therefore in a further aspect of the invention there is provided a compound of formula (I) (as depicted herein above) wherein:

$R^1$ is cyclopropyl;
$R^2$ is hydrogen;
$R^3$ is selected from fluoro, chloro or bromo;
$R^4$ is selected from methyl;
$R^5$ is fluoro;
n=1;
or a pharmaceutically acceptable salt thereof.

In another aspect of the invention, preferred compounds of the invention are any one of the Examples or a pharmaceutically acceptable salt thereof.

In another aspect of the invention, particular compounds of the invention are any one of Examples 1, 2, 6, 7, 8, 17, 18, 19, 20 or 35 or a pharmaceutically acceptable salt thereof.

In an additional embodiment the present invention provides a compound of formula (I), or a pharmaceutically acceptable salt thereof, for use as a medicament.

In an additional embodiment the present invention provides a compound of formula (I), or a pharmaceutically acceptable salt thereof, for use in the manufacture of a medicament for use in the inhibition of Trk activity.

In an additional embodiment the present invention provides a compound of formula (I), or a pharmaceutically acceptable salt thereof, for use in the manufacture of a medicament for use in the treatment or prophylaxis of cancer.

In an additional embodiment the present invention provides a compound of the formula (I), or a pharmaceutically acceptable salt thereof, for use in the manufacture of a medicament for use in the treatment of cancer in a warm-blooded animal such as man.

In an additional embodiment the present invention provides a compound of the formula (I), or a pharmaceutically acceptable salt thereof, for use in the manufacture of a medicament for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the manufacture of a medicament for use in the production of an anti-proliferative effect.

In an additional embodiment the present invention provides a method of inhibiting Trk activity comprising administering to a host in need of such treatment a therapeutically effective amount of a compound of formula (I), or a pharmaceutically acceptable salt thereof.

In an additional embodiment the present invention provides a method for the treatment of cancer comprising administering to a host in need of such treatment a therapeutically effective amount of a compound of formula (I), or a pharmaceutically acceptable salt thereof.

In an additional embodiment the present invention provides a method for the treatment or prophylaxis of cancer comprising administering a therapeutically effective amount of a compound of formula (I) or a pharmaceutically acceptable salt thereof.

In an additional embodiment the present invention provides a method for the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man comprising administering a therapeutically effective amount of a compound of formula (I) or a pharmaceutically acceptable salt thereof.

In an additional embodiment the present invention provides a method of producing an anti-proliferative effect in a warm-blooded animal, such as man, in need of such treatment which comprises administering to said animal an effective amount of a compound of formula (I), or a pharmaceutically acceptable salt thereof.

In an additional embodiment the present invention provides a pharmaceutical composition comprising a compound of formula (I), or a pharmaceutically acceptable salt thereof, together with at least one pharmaceutically acceptable carrier, diluent or excipient.

In an additional embodiment the present invention provides a pharmaceutical composition comprising a compound of formula (I), or a pharmaceutically acceptable salt thereof, together with at least one pharmaceutically acceptable carrier, diluent or excipient for use in the inhibition of Trk activity.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

In an additional embodiment the present invention provides a pharmaceutical composition comprising a compound of formula (I), or a pharmaceutically acceptable salt thereof, together with at least one pharmaceutically acceptable carrier, diluent or excipient for use in the production of an antiproliferative effect in a warm-blooded animal such as man.

In an additional embodiment the present invention provides a compound of formula (I), or a pharmaceutically acceptable salt thereof, for use in the inhibition of Trk activity.

In an additional embodiment the present invention provides a compound of formula (I), or a pharmaceutically acceptable salt thereof, for use in the treatment or prophylaxis of cancer.

In an additional embodiment the present invention provides a compound of the formula (I), or a pharmaceutically acceptable salt thereof, for use in the treatment of cancer in a warm-blooded animal such as man.

In an additional embodiment the present invention provides a compound of the formula (I), or a pharmaceutically acceptable salt thereof, for use in the treatment or prophylaxis of cancers (solid tumours and leukaemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the production of an antiproliferative effect.

In one embodiment where the inhibition of Trk activity is referred to particularly this refers to the inhibition of Trk A activity.

In another embodiment where the inhibition of Trk activity is referred to particularly this refers to the inhibition of Trk B activity.

Where the treatment (or prophylaxis) of cancer is referred to, particularly it refers to the treatment (or prophylaxis) of mesoblastic nephroma, mesothelioma, acute myeloblastic leukemia, acute lymphocytic leukemia, multiple myeloma, oesophageal cancer, myeloma, hepatocellular, pancreatic, cervical cancer, Ewings sarcoma, neuroblastoma, kaposis sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma, leukaemia, tumours of the central and peripheral nervous system, melanoma, fibrosarcoma including congenital fibrosarcoma and osteosarcoma. More particularly it refers to prostate cancer. In addition, more particularly it refers to SCLC, NSCLC, colorectal cancer, ovarian cancer and/or breast cancer. In a further aspect it refers to hormone refractory prostate cancer.

In a further aspect of the present invention provides a process for preparing a compound of formula (I) or a pharmaceutically acceptable salt thereof which process (wherein variable groups are, unless otherwise specified, as defined in formula (I)) comprises of:

Process a) Reaction of a Pyrimidine of Formula (II):

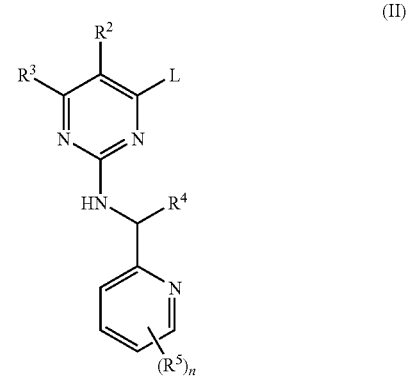

wherein L is a displaceable group; with a pyrazole amine of formula (III):

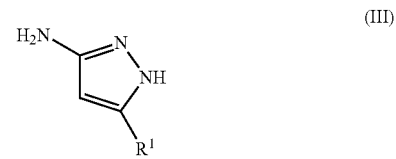

or

Process b) Reacting a Pyrimidine of Formula (Iv):

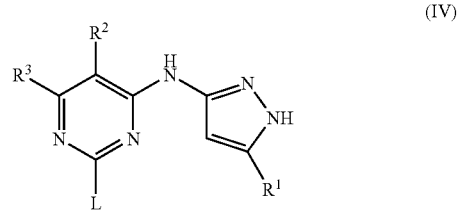

wherein L is a displaceable group; with a compound of formula (V):

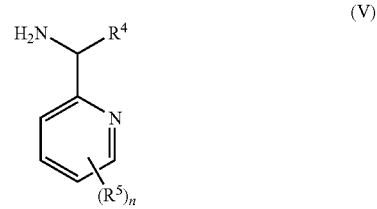

Process c) Reacting a Compound of Formula (VI):

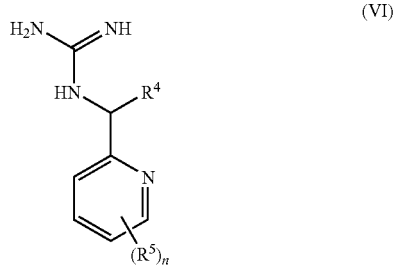

with a compound of formula (VII):

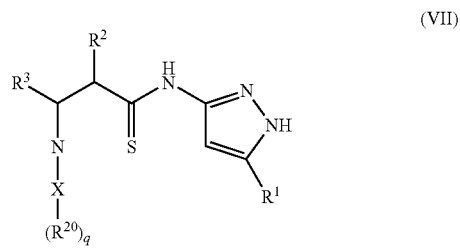

wherein X is an oxygen atom and q is 1; or X is a nitrogen atom and q is 2; and wherein each $R^{20}$ independently represents a $C_{1-6}$alkyl group; or Process d) Reacting a Compound of Formula (VIII):

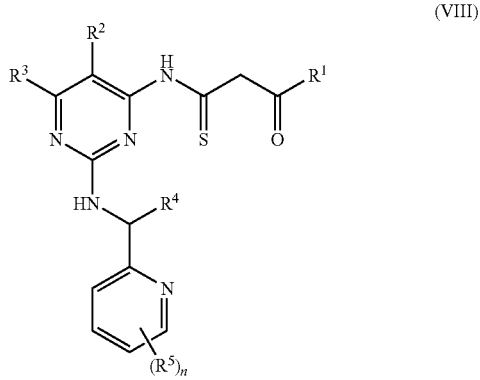

with hydrazine; or
and thereafter if necessary:
i) converting a compound of the formula (I) into another compound of the formula (I);
ii) removing any protecting groups;
iii) forming a pharmaceutically acceptable salt.

L is a displaceable group, suitable values for L are for example, a halo or sulphonyloxy group, for example a chloro, bromo, methanesulphonyloxy or toluene-4-sulphonyloxy group.

Specific reaction conditions for the above reactions are as follows.

Process a) Pyrimidines of Formula (II) and Pyrazole Amine of Formula (III) May be reacted together:
a) in the presence of a suitable solvent for example a ketone such as acetone or an alcohol such as ethanol or butanol or an aromatic hydrocarbon such as toluene or N-methyl pyrrolid-2-one, optionally in the presence of a suitable acid for example an inorganic acid such as hydrochloric acid or sulphuric acid, or an organic acid such as acetic acid or formic acid (or a suitable Lewis acid) and at a temperature in the range from 0° C. to reflux, particularly reflux; or
b) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range from 25 to 80° C.

Pyrimidines of the formula (II) may be prepared according to Scheme 1:

Scheme 1

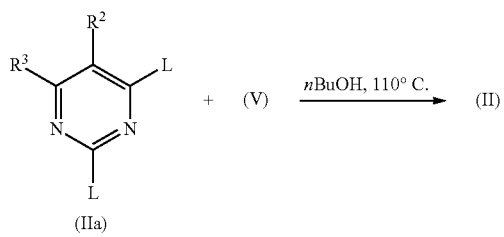

wherein L is a displaceable group as defined herein above.

Pyrazole amines of formula (III) and compounds of formula (IIa) are commercially available compounds, or they are known in the literature, or they are prepared by standard processes known in the art.

Process b) Compounds of Formula (IV) and Formula (V) May be Reacted Together Under the Same Conditions as Outlined in Process a).

Compounds of the formula (IV) may be prepared according to Scheme 2:

Scheme 2

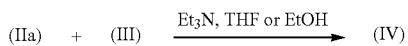

Compounds of the formula (V) are commercially available compounds, or they are known in the literature, or they are prepared by standard processes known in the art.

Process c) may conveniently be carried out in a suitable solvent such as N-methylpyrrolidinone or butanol at a temperature in the range from 100-200° C., in particular in the range from 150-170° C. The reaction is preferably conducted in the presence of a suitable base such as, for example, sodium methoxide or potassium carbonate.

Compounds of the formula (VI) may be prepared according to Scheme 3:

Scheme 3

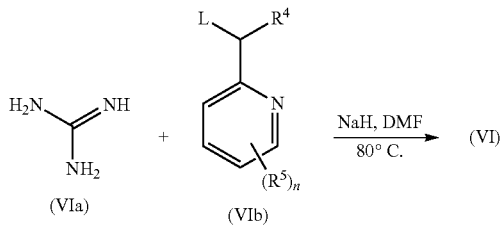

Compounds of the formula (VII) may be prepared according to Scheme 4:

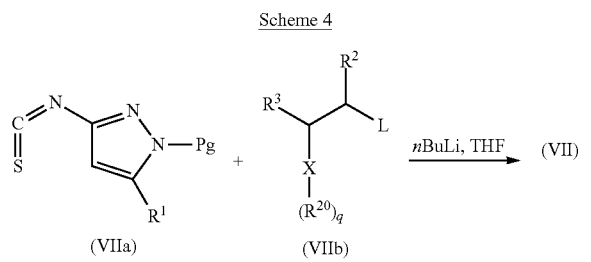

wherein Pg is a suitable nitrogen protecting group. Suitable values for Pg are defined below.

Compounds of the formula (VIa), (VIb), (VIla) and (VIIb) are commercially available compounds, or they are known in the literature, or they are prepared by standard processes known in the art.

Process d) may be carried out in a suitable solvent, for example, an alcohol such as ethanol or butanol at a temperature in the range from 50-120° C., in particular in the range from 70-100° C.

Compounds of the formula (VIII) may be prepared according to Scheme 5:

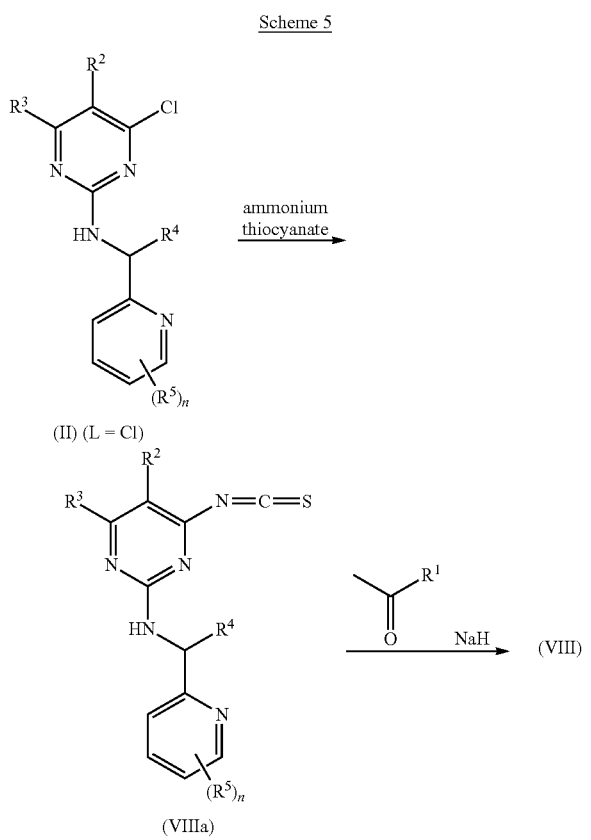

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

DEFINITIONS

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl. However, references to individual alkyl groups such as 'propyl' are specific for the straight-chained version only and references to individual branched chain alkyl groups such as 'isopropyl' are specific for the branched-chain version only. A similar convention applies to other radicals. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)—, and a ring sulphur atom may be optionally oxidised to form the S-oxides. Examples and suitable values of the term "heterocyclyl" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Further examples and suitable values of the term "heterocyclyl" are morpholino, piperazinyl and pyrrolidinyl. In one aspect of the invention a "heterocyclyl" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides.

A "3-5-membered heterocyclyl" is a saturated, partially saturated or unsaturated, monocyclic ring containing 3, 4 or 5 atoms of which at least one atom is chosen from nitrogen, sulphur or oxygen, which may, unless otherwise specified, be carbon or nitrogen linked, wherein a —$CH_2$— group can optionally be replaced by a —C(O)—, and a ring sulphur atom may be optionally oxidised to form the S-oxides. Examples and suitable values of the term "3-5-membered heterocyclyl" are pyrrolyl, pyrrolinyl, imidazolyl, thiazolyl and furanyl.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl.

A "3-5-membered carbocyclyl" is a saturated, partially saturated or unsaturated, monocyclic carbon ring that contains 3, 4 or 5 atoms; wherein a —$CH_2$— group can optionally be replaced by a —C(O)—. Suitable values for "3-5-membered carbocyclyl" include cyclopropyl, cyclobutyl, 1-oxocyclopentyl, cyclopentyl or cyclopentenyl.

The term "$C_{m-n}$" or "$C_{m-n}$group" used alone or as a prefix, refers to any group having m to n carbon atoms.

The term "optionally substituted" refers to either groups, structures, or molecules that are substituted and those that are not substituted.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, $C_{1-3}$alkoxy, methoxy, ethoxy and propoxy. Examples of "$C_{1-6}$alkoxyimino" include $C_{1-4}$alkoxyimino, $C_{1-3}$alkoxyimino, methoxyimino, ethoxyimino and propoxyimino Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$alkylthio" include methylthio and ethylthio. Examples of "$C_{1-6}$alkylsulphonylamino" include methylsulphonylamino and ethylsulphsulphonylamino. Examples of "$C_{1-6}$alkanoyl" include $C_{1-4}$alkanoyl, propionyl and acetyl. Examples of "N—($C_{1-6}$alkyl)amino" include methylamino and ethylamino. Examples of "N,N—($C_{1-6}$alkyl)$_2$-amino" include di-N-methylamino, di-(N-ethyl) amino and N-ethyl-N-methylamino. Examples of "$C_{2-6}$alkenyl" are vinyl, allyl and 1-propenyl. Examples of "$C_{2-6}$alkynyl" are ethynyl, 1-propynyl and 2-propynyl. Examples of "N—($C_{1-6}$alkyl)sulphamoyl" are N-(methyl)sulphamoyl and N-(ethyl)sulphamoyl. Examples of "N—($C_{1-6}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" are N—($C_{1-4}$alkyl)carbamoyl, methylaminocarbonyl and ethylaminocarbonyl. Examples of "N,N—($C_{1-6}$alkyl)$_2$-carbamoyl" are N,N—($C_{1-4}$alkyl)$_2$-carbamoyl, dimethylaminocarbonyl and methylethylaminocarbonyl.

"RT" or "rt" means room temperature.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine. In a further aspect of the invention, a suitable pharmaceutically acceptable salt of a compound of the inventions, particularly a compound selected from any one of the Examples, is a salt formed with an acid selected from: benzoic acid, 2-(benzoylamino)acetic acid, 1,2-ethane disulfonic acid, fumaric acid, maleic acid, mandalic acid, naphthalene-1,5-disulfonic acid, phosphoric acid, succinic acid, sulfuric acid or undec-10-enoic acid. In one aspect the salt is a phosphate. In another aspect the salt is a sulphate. In a further aspect the salt is a fumarate. In a further aspect the salt is a maleate.

It should be noted that the compounds claimed in this invention are capable of existing in different resonance structures and thus the compounds claimed herein include all possible resonance structures, for example optical isomers, diastereoisomers and geometric isomers and all tautomeric forms of the compounds of the formula (I).

It is also to be understood that certain compounds of the formula (I) can exist in solvated as well as unsolvated forms such as, for example, hydrated forms. It is to be understood that the invention encompasses all such solvated forms.

Formulations

Compounds of the present invention may be administered orally, parenteral, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of cancer is an amount sufficient to symptomatically relieve in a warm-blooded animal, particularly a human the symptoms of cancer, to slow the progression of cancer, or to reduce in patients with symptoms of cancer the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substance, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Combinations

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb 1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as
N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and
6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies; and (x) other treatment regimes including: dexamethasone, proteasome inhibitors (including bortezomib), isotretinoin (13-cis retinoic acid), thalidomide, revemid, Rituxamab, ALIMTA, Cephalon's kinase inhibitors CEP-701 and CEP-2563, anti-Trk or anti-NGF monoclonal antibodies, targeted radiation therapy with 131I-metaiodobenzylguanidine (131I-MIBG), anti-G(D2) monoclonal antibody therapy with or without granulocyte-macrophage colony-stimulating factor (GM-CSF) following chemotherapy.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically-active agent within its approved dosage range.

Synthesis

The compounds, or pharmaceutically acceptable salts thereof, of the present invention can be prepared in a number of ways well known to one skilled in the art of organic synthesis. The compounds, or pharmaceutically acceptable salts thereof, of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds, or pharmaceutically acceptable salts thereof, of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;

(ii) organic solutions were dried over anhydrous magnesium sulfate; evaporation of organic solvent was carried out using a rotary evaporator under reduced pressure (4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC or liquid chromatography/mass spectroscopy (LC/MS) and reaction times are given for illustration only;

(v) final products have satisfactory proton nuclear magnetic resonance (NMR) spectra and/or mass spectra data;

(vi) yields are given for illustration only and are not necessarily those which can be obtained by diligent process development; preparations were repeated if more material was required;

(vii) when given, NMR data is in the form of delta values for major diagnostic protons, given in part per million (ppm) relative to tetramethylsilane (TMS) as an internal standard, determined at 300 MHz in DMSO-$d_6$ unless otherwise stated;

(viii) chemical symbols have their usual meanings;

(ix) solvent ratio was given in volume:volume (v/v) terms.

(x) the following abbreviations have been used:

| DIEA | N,N-diisopropylethylamine; |
|---|---|
| DMF | N,N-dimethylformamide; |
| THF | tetrahydrofuran; |
| DCM | dichloromethane; |
| DMAP | 4-dimethylaminopyridine; |
| TMSCl | trimethylsilylchloride; |
| EtOAc | ethyl acetate; |
| TMSI | trimethylsilyl imidazole; |

(xi) an Argonaut Endeaver reactor refers to a parallel, multi-reactor synthesizer for pressurized reactions available from Argonaut Technologies Limited; New Road, Hengoed, Mid Glamorgan; United Kingdom, CF82 8AU;

(xii) Where a Biotage cartridge/column is referred to, this means a pre-packed chromatography cartridge for separation of compounds in a mixture, i.e. a polypropylene tube containing silica gel, used according to the manufacturers instructions obtained from Biotage UK Ltd., Harforde Court, Foxholes Business Park, John Tate Road, Hertford, SG13 7NW, United Kingdom; and (xiii) an ISCO Combiflash refers to flash chromatography on silica gel using Isco Combiflash® separation system: RediSep normal phase flash column, flow rate, 30-40 ml/min.

Example 1

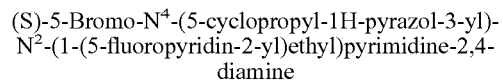

(S)-5-Bromo-$N^4$-(5-cyclopropyl-1H-pyrazol-3-yl)-$N^2$-(1-(5-fluoropyridin-2-yl)ethyl)pyrimidine-2,4-diamine A mixture of 5-bromo-2-chloro-N-(3-cyclopropyl-1H-pyrazol-5-yl)pyrimidin-4-amine (Method 8; 0.062 g, 0.196 mmol), (S)-1-(5-fluoropyridin-2-yl)ethanamine (Method 6; 0.025 g, 0.178 mmol), and DIEA (0.04 ml, 0.214 mmol) in n-BuOH (2 ml) was heated in a sealed tube at 175° C. for 20 hours. The solvent was removed under reduced pressure and the residue was purified by column chromatography (hexane: EtOAc=1:1) to give the title compound as a white solid (0.064 g, 86%). $^1$H NMR (400 MHz) 12.48 and 12.09 (s, 1H), 9.32 (s, 1H), 8.48 (d, J=2.4 Hz, 1H), 8.00 (b, 1H), 7.92 (s, 1H), 7.64 (m, 1H), 7.41 (m, 1H), 5.94 and 5.85 (b, 1H), 5.06 (m, 1H), 1.84 (m, 1H), 1.45 (d, J=7.2 Hz, 3H), 0.95 (m, 1H), 0.86 (m, 1H), 0.74 (m, 1H), 0.63 (m, 1H). MS: Calcd.: 417. Found: [M+H]$^+$418.

Example 2

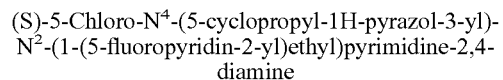

(S)-5-Chloro-$N^4$-(5-cyclopropyl-1H-pyrazol-3-yl)-$N^2$-(1-(5-fluoropyridin-2-yl)ethyl)pyrimidine-2,4-diamine A mixture of 2,5-dichloro-4-(5-cyclopropyl-1H-pyrazole-3-ylamino)pyrimidine (Method 7; 0.064 g, 0.235 mmol), (S)-1-(5-fluoropyridin-2-yl)ethanamine (Method 6; 0.030 g, 0.214 mmol), and DIEA (0.045 ml, 0.257 mmol) in n-BuOH (2 ml) was heated in a sealed tube at 175° C. for 20 hours. The solvent was removed under reduced pressure and the residue was purified by column chromatography (hexane:EtOAc=1:1) to give the title compound as a white solid (0.060 g, 75%). $^1$H NMR (400 MHz) 12.51 and 12.09 (s, 1H), 9.70 and 9.64 (s, 1H), 8.49 (s, 1H), 8.38 (s, 1H), 8.02 and 7.93 (b, 1H), 7.63 (m, 1H), 7.40 (m, 1H), 5.93 and 5.80 (s, 1H), 5.06 (m, 1H), 1.83 (m, 1H), 1.45 (d, J=6.8 Hz, 3H), 0.94 (m, 1H), 0.84 (m, 1H), 0.74 (m, 1H), 0.63 (m, 1H). MS: Calcd.: 373. Found: [M+H]$^+$374.

Example 3

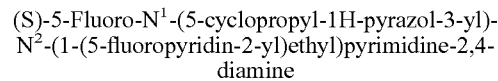

(S)-5-Fluoro-$N^1$-(5-cyclopropyl-1H-pyrazol-3-yl)-$N^2$-(1-(5-fluoropyridin-2-yl)ethyl)pyrimidine-2,4-diamine A mixture of 2-chloro-N-(3-cyclopropyl-1H-pyrazol-5-yl)-5-fluoropyrimidin-4-amine (Method 9; 0.200 g, 0.788 mmol), (S)-1-(5-fluoropyridin-2-yl)ethanamine (Method 6; 0.116 g, 0.828 mmol), and DIEA (0.17 ml, 0.946 mmol) in n-BuOH (2 ml) was heated in a sealed tube at 175° C. for 40 hours. The solvent was removed under reduced pressure and the residue was purified by column chromatography (hexane: EtOAc=1:1) to give the title compound as a white solid (0.175 g, 62%). $^1$H NMR (400 MHz) 12.47 and 11.98 (s, 1H), 10.15 and 9.27 (s, 1H), 8.48 (s, 1H), 7.89 and 7.81 (s, 1H), 7.65 (m, 1H), 7.42 (b, 1H), 7.20 (b, 1H), 5.76 and 5.64 (s, 1H), 5.00 (m, 1H), 1.85 (m, 1H), 1.44 (d, J=6.8 Hz, 3H), 0.95 (m, 1H), 0.85 (m, 1H), 0.74 (m, 1H), 0.63 (m, 1H). MS: Calcd.: 357. Found: [M+H]$^+$358.

Example 4

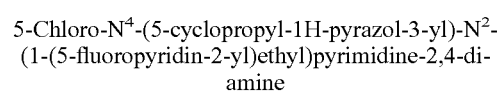

5-Chloro-$N^4$-(5-cyclopropyl-1H-pyrazol-3-yl)-$N^2$-(1-(5-fluoropyridin-2-yl)ethyl)pyrimidine-2,4-diamine A mixture of 2,5-dichloro-4-(5-cyclopropyl-1H-pyrazole-3-ylamino)pyrimidine (Method 7; 0.14 g, 0.518 mmol), 1-(5- fluoropyridin-2-yl)ethanamine (Method 4; 0.091 g, 0.648 mmol), and DIEA (0.11 ml, 0.648 mmol) in n-BuOH (2 ml) was heated in a sealed tube at 185° C. for 18 hours. The solvent was removed under reduced pressure and the residue was purified by column chromatography (hexane-EtOAc=1: 2) to give the title compound as a white solid (0.070 g, 36%). $^1$H NMR (400 MHz) 12.51 and 12.09 (s, 1H), 9.65 (s, 1H), 8.48 (s, 1H), 8.38 (s, 1H), 8.02 and 7.93 (b, 1H), 7.64 (m, 1H), 7.41 (m, 1H), 5.93 and 5.80 (b, 1H), 5.06 (m, 1H), 1.83 (m, 1H), 1.45 (d, J=6.8 Hz, 3H), 0.95 (m, 1H), 0.84 (m, 1H), 0.74 (m, 1H), 0.63 (m, 1H). MS: Calcd.: 373. Found: [M+H]$^+$374.

Example 5

5-Chloro-N$^4$-(5-cyclopropyl-1H-pyrazol-3-yl)-N$^2$-[1-(5-fluoro-6-methylpyridin-2-yl)ethyl]pyrimidine-2,4-diamine A microwave reaction vessel was charged with [1-(5-fluoro-6-methylpyridin-2-yl)ethyl]amine (Method 13; 159 mg, 1.03 mmol), 2,5-dichloro-4-(5-cyclopropyl-1H-pyrazole-3-ylamino)pyrimidine (Method 7; 335 mg, 1.24 mmol) and DIEA (0.35 ml, 2.0 mmol). Anhydrous n-BuOH (1.5 ml) was added, and the tube was sealed and heated in a microwave reactor at 175° C. for 10 hours. The resulting mixture was partitioned between EtOAc and H$_2$O. The aqueous layer was extracted with EtOAc, and the combined organics were washed with brine, dried, filtered, chromatography (R$_f$ in 50:50 hexanes:EtOAc=0.25) to afford the title compound as a colourless solid (110 mg, 28%). $^1$H NMR (400 MHz, CDCl$_3$) δ 0.65-0.75 (m, 2H), 0.85-0.95 (m, 2H), 1.47 (d, J=6.8 Hz, 3H), 1.82 (tt, J=8.5, 5.1 Hz, 1H), 2.46 (d, J=2.8 Hz, 3H), 4.99-5.09 (m, 1H), 6.01 (s, 1H), 6.26 (s, 1H), 7.05 (dd, J=8.3, 3.5 Hz, 1H), 7.15-7.23 (m, 1H), 7.38-7.48 (m, 1H), 7.84 (s, 1H). Calcd.: 387. Found [M+H$^+$] 388.

Example 6

5-Chloro-N$^2$-[(1S)-1-(5-fluoropyridin-2-yl)ethyl]-N$^4$-(5-isopropoxy-1H-pyrazol-3-yl)pyrimidine-2,4-diamine To a suspension of 2,5-dichloro-N-(5-isoproxy-1H-pyrazol-3-yl)pyrimidin-4-amine (Method 10; 3.59 g, 12.48 mmol) and (S)-1-(5-fluoropyridin-2-yl)ethanamine (Method 6; 1.75 g, 12.48 mmol) in 1-butanol (15 ml) contained in a microwave vial was added DIEA (3.86 g, 29.96 mmol). The vial was mounted onto the microwave reactor and the reaction was run at 160° C. for 10 hours. The solvent was evaporated off and the residue diluted with EtOAc (125 ml). The solution was washed with brine twice (2×40 ml). The organic layer was obtained and evaporated to dryness. The dried residue was dissolved in minimum amount of EtOAc and subject to silica gel chromatographic purification (by ISCO Combiflash with gradient EtOAc/hexanes) to give the title compound. LC-MS, 393 (M+1); $^1$H NMR (CDCl$_3$) δ 8.45 (s, 1H), 7.90 (s, 1H), 7.35 (d, 2H), 6.30 (br s, 1H), 5.40 (s, 1H), 5.15 (m, 1H), 4.80 (m, 1H), 1.60 (d, 3H), 1.35 (d, 6H).

Example 7-10

The following compounds were prepared by the procedure similar to that of Example 6 using an appropriate pyrimidine and (S)-1-(5-fluoropyridin-2-yl)ethanamine (Method 6).

| Ex. | Compound | NMR and/or LC/MS | SM |
|---|---|---|---|
| 7 | 5-Fluoro-N$^2$-[(1S)-1-(5-fluoropyridin-2-yl)ethyl]-N$^4$-(5-isopropoxy-1H-pyrazol-3-yl)pyrimidine-2,4-diamine | LC-MS, 376 (M + 1); $^1$H NMR (CDCl$_3$) δ 8.55 (s, 1H), 7.91 (d, 1H), 7.50 (m, 2H), 5.71 (s, 1H), 5.25 (m, 1H), 4.95 (m, 1H), 1.75 (d, 3H), 1.55 (d, 6H) | Method 11 |
| 8 | (S)-5-Bromo-N$^2$-(1-(5-fluoropyridin-2-yl)ethyl)-N$^4$-(5-isopropoxy-1H-pyrazol-3-yl)pyrimidine-2,4-diamine | LC-MS, 436 (M + 1); $^1$H NMR (400 MHz) δ 11.96 (s, 1H), 9.37 (s, 1H), 8.50 (s, 1H), 8.02 (br s, 2H), 7.66 (m, 1H), 7.43 (m, 1H), 5.58 (s, 1H), 5.07 (br s, 1H), 4.68 (m, 1H), 1.46 (d, J = 6.8 Hz, 3H), 1.28 (d, J = 6.0 Hz, 6H) | Method 12 |
| 9 | (S)-2-(5-Chloro-2-(1-(5-fluoropyridin-2-yl)ethylamino)-6-(5-isopropoxy-1H-pyrazol-3-ylamino)pyrimidin-4-ylamino)propane-1,3-diol | LC-MS, 481 (M + 1); $^1$H NMR (400 MHz) δ 11.90 (s, 1H), 9.04 (s, 1H), 8.47 (s, 1H), 7.64 (m, 2H), 7.44 (m, 1H), 5.67 (d, J = 7.2 Hz, 1H), 5.36 (d, J = 1.6 Hz, 1H), 5.00 (m, 1H), 4.62-4.69 (m, 2H), 4.55 (m, 1H), 3.87 (m, 1H), 3.56 (m, 1H), 3.48 (m, 1H), 3.32 (m, 1H), 3.23 (m, 1H), 1.44 (d, J = 7.2 Hz, 3H), 1.26 (d, J = 6.0 Hz, 6H) | Example 30 |
| 10 | (R)-3-(5-Chloro-2-((S)-1-(5-fluoropyridin-2-yl)ethylamino)-6-(5-isopropoxy-1H-pyrazol-3-ylamino)pyrimidin-4-ylamino)propane-1,2-diol | $^1$H NMR (400 MHz) δ 11.91 (s, 1H), 9.02 (s, 1H), 8.47 (s, 1H), 7.64 (m, 2H), 7.43 (m, 1H), 6.24 (t, J = 5.6 Hz, 1H), 5.37 (d, J = 1.6 Hz, 1H), 4.99 (m, 1H), 4.72 (m, 1H), 4.65 (m, 1H), 4.55 (m, 1H), 3.43 (m, 1H), 3.37 (m, 1H), 3.26 (m, 2H), 3.10 (m, 1H), 1.43 (d, J = 6.8 Hz, 3H), 1.26 (d, J = 6.0 Hz, 6H); LC-MS, 481 (M + 1) | Example 30 |

Example 6

Alternative Procedure

5-Chloro-N$^2$-[(1S)-1-(5-fluoropyridin-2-yl)ethyl]-N$^4$-(5-isopropoxy-1H-pyrazol-3-yl)pyrimidine-2,4-diamine To a suspension of 2,5-dichloro-N-(5-isoproxy-1H-pyrazol-3-yl)pyrimidin-4-amine (Method 10; 67.4 g, 0.24 mol) and (S)-1-(5-fluoropyridin-2-yl)ethanamine (Method 6; 64.8 g, 0.3 mmol) in n-butanol (283 ml) was added DIEA (203 ml, 1.17 mol) and the mixture was heated to reflux (~115° C.) and stirred overnight. The mixture was concentrated to a foam. This was added to EtOAc (1.5 l). The solution was washed with water (200 ml) and brine (200 ml), dried over sodium sulphate, filtered and concentrated to a foam, 100 g. This was purified by column chromatography (40% EtOAc/60% iso-hexane). The product was dried overnight in a vacuum oven at 45° C. to give 80 g of solid. This solid was purified by chromatography (1:1 EtOAc:DCM). The isolated solid was dried for 36 hours in a vacuum oven at 45° C. to give a foam 53 g.

Example 11

(2S)-3-({5-Fluoro-2-{[(1S)-1-(5-fluoropyridin-2-yl)ethyl]amino}-6-[(5-isopropoxy-1H-pyrazol-3-yl)amino]pyrimidin-4-yl}oxy)propane-1,2-diol To a solution of 6-{[(4R)-2,2-dimethyl-1,3-dioxolan-4-yl]methoxy}-5-fluoro-N$^2$-[(1S)-1-(5-fluoropyridin-2-yl)ethyl]-N$^4$-(5-isopropoxy-1H-pyrazol-3-yl)pyrimidine-2,4-diamine (Example 25; 0.21 g, 0.415 mmol) in methanol (5 ml) was added a few drops of water and then p-toluenesulfonic acid (0.119 g, 0.623 mmol). The mixture was stirred at room temperature for 16 hours. The solvent was removed in vacuo and the residue was subjected to silica gel chromatographic purification (by ISCO Combiflash with gradient EtOAc/hexanes) to afford the desired product as a white solid (0.075 g, yield 40%). LC-MS, 466 (M+1); $^1$H NMR δ 9.85 (br s, 1H), 8.30 (s, 1H), 7.60 (m, 1H), 7.30 (m, 1H), 5.25 (s, 1H), 4.80-4.90 (m, 2H), 4.60 (m, 2H), 4.0 (br s, 2H), 3.55 (m, 1H), 1.35 (d, 3H), 1.15 (d, 6H).

Example 12-15

The following compounds were prepared by the procedure similar to that of Example 11 using an appropriate pyrimidine.

| Ex. | Compound | NMR and/or LC/MS | SM |
|---|---|---|---|
| 12 | 2-({5-Fluoro-2-{[(1S)-1-(5-fluoropyridin-2-yl)ethyl]amino}-6-[(5-isopropoxy-1H-pyrazol-3-yl)amino]pyrimidin-4-yl}oxy)propane-1,3-diol | LC-MS, 466 (M + 1); $^1$H NMR δ 9.85 (br s, 1H), 8.44 (s, 1H), 7.60 (d, 1H), 7.40 (d, 1H), 5.20 (s, 1H), 4.85 (m, 2H), 4.75 (m, 1H), 4.55 (m, 1H), 3.54 (m, 1H), 1.40 (d, 3H), 1.20 (d, 6H) | Example 26 |
| 13 | (S)-2-(5-Chloro-2-(1-(5-fluoropyridin-2-yl)ethylamino)-6-(5-isopropoxy-1H-pyrazol-3-ylamino)pyrimidin-4-yloxy)propane-1,3-diol | $^1$H NMR (400 MHz) δ 11.90 (s, 1H), 9.36 (s, 1H), 8.49 (s, 1H), 7.98 (d, J = 7.2 Hz, 1H), 7.66 (m, 1H), 7.43 (m, 1H), 5.45 (s, 1H), 4.97 (m, 1H), 4.71 (m, 1H), 4.64 (m, 1H), 4.56 (m, 1H), 3.43 (m, 1H), 3.61 (m, 2H), 3.30 (m, 2H), 1.46 (d, J = 7.2 Hz, 3H), 1.27 (d, J = 6.0 Hz, 6H); LC-MS, 482 (M + 1) | Example 27 |
| 14 | (S)-2-(2-(1-(5-Fluoropyridin-2-yl)ethylamino)-6-(5-isopropoxy-1H-pyrazol-3-ylamino)pyrimidin-4-yloxy)propane-1,3-diol | $^1$H NMR (400 MHz) δ 11.91 (s, 1H), 9.38 (s, 1H), 8.49 (s, 1H), 8.00 (d, J = 7.2 Hz, 1H), 7.65 (m, 1H), 7.45 (m, 1H), 5.45 (s, 1H), 5.02 (m, 1H), 4.82 (d, J = 4.8 Hz, 1H), 4.66 (m, 1H), 4.61 (m, 1H), 4.08 (m, 2H), 3.63 (m, 1H), 3.30 (m, 2H), 1.46 (d, J = 6.8 Hz, 3H), 1.27 (d, J = 6.0 Hz, 6H); LC-MS, 448 (M + 1) | [1] |
| 15 | (S)-3-(5-Chloro-2-((S)-1-(5-fluoropyridin-2-yl)ethylamino)-6-(5-isopropoxy-1H-pyrazol-3-ylamino)pyrimidin-4-yloxy)propane-1,2-diol | $^1$H NMR (400 MHz) δ 11.91 (s, 1H), 9.38 (s, 1H), 8.49 (s, 1H), 8.00 (d, J = 7.2 Hz, 1H), 7.65 (m, 1H), 7.45 (m, 1H), 5.45 (s, 1H), 5.02 (m, 1H), 4.82 (d, J = 4.8 Hz, 1H), 4.66 (m, 1H), 4.61 (m, 1H), 4.08 (m, 2H), 3.63 (m, 1H), 3.30 (m, 2H), 1.46 (d, J = 6.8 Hz, 3H), 1.27 (d, J = 6.0 Hz, 6H); LC-MS, 482 (M + 1) | Example 28 |

[1] Obtained as a by-product from Example 13

Example 16

(S)-5-Chloro-N²-(1-(5-fluoropyridin-2-yl)ethyl)-N⁴-(5-isopropoxy-1H-pyrazol-3-yl)pyrimidine-2,4,6-triamine (S)-5,6-Dichloro-N²-(1-(5-fluoropyridin-2-yl)ethyl)-N⁴-(5-isopropoxy-1H-pyrazol-3-yl)pyrimidine-2,4-diamine (Example 30, 0.100 g, 0.469 mmol) was mixed with n-butanol (1.75 ml) and ammonium hydroxide (1.75 ml, 28.2 mmol) in an Argonaut Endeaver reactor. This was sealed and heated to 165° C. for 48 hours. The solvent was removed under reduced pressure and the resulted residue was purified by reverse phase Biotage chromatography to give the title compound as a brownish solid (0.045 g, 24%). ¹H NMR (400 MHz) δ 11.92 (s, 1H), 9.03 (s, 1H), 8.49 (s, 1H), 7.66 (m, 1H), 7.52 (s, 1H), 7.46 (m, 1H), 6.32 (s, 2H), 5.38 (s, 1H), 5.05 (s, 1H), 4.65 (m, 1H), 1.43 (d, J=7.2 Hz, 3H), 1.26 (d, J=6.0 Hz, 6H). MS: Calcd.: 406. Found: [M+H]⁺ 407.

Example 17

(S)-5-Chloro-N⁴-(5-cyclopropyl-1H-pyrazol-3-yl)-N²-(1-(3,5-difluoropyridin-2-yl)ethyl)pyrimidine-2,4-diamine A mixture of 2,5-dichloro-N-(5-cyclopropyl-1H-pyrazol-3-yl)pyrimidin-4-amine (Method 7; 0.18 g, 0.666 mmol), (S)-1-(3,5-difluoropyridin-2-yl)ethanamine (Method 21; 0.132 g, 0.833 mmol), and DIEA (0.139 ml, 0.800 mmol) in n-BuOH (2 ml) was heated in a sealed tube at 175° C. for 17 hours. The solvent was removed under reduced pressure and the residue was purified by column chromatography (hexane:EtOAc=1.5:1) to give the title compound as a white solid (0.21 g, 80%). ¹H NMR (400 MHz) δ 12.50 and 12.09 (s, 1H), 9.60 and 8.50 (s, 1H), 8.43 and 8.35 (s, 1H), 7.88-8.04 (m, 3H), 7.26 (br, 1H), 5.33 (m, 1H), 1.88 (m, 1H), 1.36 (d, J=6.8 Hz, 3H), 0.94 (m, 1H), 0.86 (m, 1H), 0.74 (m, 1H), 0.62 (m, 1H). MS: Calcd.: 391. Found: [M+H]⁺ 392.

Example 18-21

The following compounds were prepared by the procedure similar to that of Example 17 using an appropriate pyrimidine (method to prepare which is also listed) and an amine.

| Ex. | Compound | NMR and/or LC/MS | SM |
|---|---|---|---|
| 18 | (S)-5-Chloro-N²-(1-(3,5-difluoropyridin-2-yl)ethyl)-N⁴-(5-isopropoxy-1H-pyrazol-3-yl)pyrimidine-2,4-diamine | 1H NMR (400 MHz) δ 11.99 (s, 1H), 9.63 (s, 1H), 8.47 (s, 1H), 8.07 (d, J = 7.6 Hz, 1H), 7.95 (s, 1H), 7.89 (m, 1H), 5.50 (s, 1H), 5.38 (m, 1H), 4.67 (m, 1H), 1.44 (d, J = 6.8 Hz, 3H), 1.27 (d, J = 6.0 Hz, 6H); MS: Calcd.: 409; Found: [M + H]⁺ 410 | Method 10 and Method 21 |
| 19 | (S)-5-Bromo-N²-(1-(3,5-difluoropyridin-2-yl)ethyl)-N⁴-(5-isopropoxy-1H-pyrazol-3-yl)pyrimidine-2,4-diamine | 1H NMR (400 MHz) δ 11.97 (s, 1H), 9.35 (s, 1H), 8.47 (s, 1H), 8.09 (d, J = 7.2 Hz, 1H), 8.02 (s, 1H), 7.89 (m, 1H), 5.56 (s, 1H), 5.37 (m, 1H), 4.67 (m, 1H), 1.44 (d, J = 6.8 Hz, 3H), 1.27 (d, J = 6.0 Hz, 6H); MS: Calcd.: 453; Found: [M + H]⁺ 454 | Method 12 and Method 21 |
| 20 | (S)-N²-(1-(3,5-Difluoropyridin-2-yl)ethyl)-5-fluoro-N⁴-(5-isopropoxy-1H-pyrazol-3-yl)pyrimidine-2,4-diamine | 1H NMR (400 MHz) δ 11.97 (s, 1H), 10.17 (s, 1H), 8.46 (s, 1H), 7.89 (m, 2H), 7.80 (m, 1H), 5.33 (s, 1H), 4.67 (m, 1H), 1.43 (d, J = 6.8 Hz, 3H), 1.27 (d, J = 6.0 Hz, 6H); MS: Calcd.: 393; Found: [M + H]⁺ 394 | Method 11 and Method 21 |
| 21 | 5-Chloro-N⁴-(5-cyclopropyl-1H-pyrazol-3-yl)-N²-(1-(3,5-difluoropyridin-2-yl)ethyl)pyrimidine-2,4-diamine | MS: Calcd.: 391; Found: [M + H]⁺ 392 | Method 7 and Method 36 |

Example 22

(S)-N²-(1-(5-Bromopyridin-2-yl)ethyl)-5-chloro-N⁴-(5-cyclopropyl-1H-pyrazol-3-yl)-pyrimidine-2,4-diamine A mixture of 2,5-dichloro-N-(5-cyclopropyl-1H-pyrazol-3-yl)pyrimidin-4-amine (Method 7; 0.15 g, 0.553 mmol), (S)-1-(5-bromopyridin-2-yl)ethanamine (Method 26; 0.245 g, 0.611 mmol), and DIEA (0.145 ml, 0.833 mmol) in n-BuOH (2 ml) was heated in a sealed tube at 180° C. in a microwave for 1 hour. The solvent was removed under reduced pressure and the residue was purified by column chromatography (hexane:EtOAc=1:1) to give the title compound as a white solid (0.165 g, 68%). ¹H NMR (400 MHz) δ 12.48, 12.38 and 12.07 (s, 1H), 9.66 (br s, 1H), 8.62 (s, 1H), 8.33 and 7.57 (br s, 1H), 7.96 (d, J=8.2 Hz, 1H), 7.92 (br s, 1H), 7.32 (br s, 1H), 5.81 (bs, 1H), 4.99 (br s, 1H), 1.84 (br s, 1H), 1.45 (d, J=6.8 Hz, 3H), 0.94 (m, 2H), 0.71 (m, 2H). MS: Calcd.: 435. Found: [M+11]⁺ 436.

Example 23

The following compounds were prepared by the procedure similar to that of Example 22 using an appropriate pyrimidine (method to prepare which is also listed) and an amine.

| Ex. | Compound | NMR and/or LC/MS | Method |
|---|---|---|---|
| 23 | (S)-$N^2$-(1-(5-Bromopyridin-2-yl)ethyl)-$N^4$-(5-cyclopropyl-1H-pyrazol-3-yl)-5-fluoropyrimidine-2,4-diamine | $^1$H NMR (400 MHz) δ 12.35, 12.27 and 11.99 (s, 1H), 9.28 (br s, 1H), 8.61 (s, 1H), 7.96 (d, J = 8.4 Hz, 1H), 7.82 (br s, 1H), 7.33 (d, J = 8.4 Hz, 1H), 7.24 (br s, 1H), 5.63 (br s, 1H), 4.94 (br s, 1H), 1.84 (m, 1H), 1.44 (d, J = 7.2 Hz, 3H), 0.93 (m, 2H), 0.70 (m, 2H); MS: Calcd.: 417; Found: [M + H]$^+$ 418. | Method 9 and Method 26 |

Example 24

(S)-$N^4$45-Cyclopropyl-1H-pyrazol-3-yl)-5-chloro-$N^2$-(1)-(5-cyclopropylpyridin-2-yl)ethyl)-pyrimidine-2,4-diamine A mixture of 2,5-dichloro-4-(5-cyclopropyl-1H-pyrazole-3-ylamino)pyrimidine (Method 7; 0.100 g, 0.37 mmol), (S)-1-(5-cyclopropylpyridin-2-yl)ethanamine hydrochloride (Method 30; 0.109 g, 0.463 mmol), and DIEA (0.258 ml, 1.48 mmol) in n-BuOH (2 ml) was heated in a sealed tube at 175° C. for 17 hours. The solvent was removed under reduced pressure and the residue was purified by column chromatography (hexane-EtOAc=1:2) to give the title compound as a white solid (0.105 g, 72%). $^1$H NMR (400 MHz) δ 12.51 and 12.06 (s, 1H), 9.59 (s, 1H), 8.33 (s, 1H), 8.30 (s, 1H), 7.92 (m, 1H), 7.34 (m, 1H), 7.22 (s, 1H), 5.99 and 5.80 (br, 1H), 4.99 (m, 1H), 1.89 (m, 1H), 1.84 (m, 1H), 1.43 (d, J=7.2 Hz, 3H), 0.95 (m, 2H), 0.86 (m, 21-1), 0.68 (m, 4H). MS: Calcd.: 395. Found: [M-141]$^+$ 396.

Example 25

6-{[(4R)-2,2-Dimethyl-1,3-dioxolan-4-yl]methoxy}-5-fluoro-$N^2$-[(1S)-1-(5-fluoropyridin-2-yl)ethyl]-(5-isopropoxy-1H-pyrazol-3-yl)pyrimidine-2,4-diamine Sodium hydride (0.016 g, 0.673 mmol) was added slowly to neat (R)-2,2-dimethyl-1,3-dioxolane (1.41 g, 10.66 mmol) whereupon bubbles were released to form a suspension. When bubbling stopped, 6-chloro-5-fluoro-$N^2$-[(1S)-1-(5-fluoropyridin-2-yl)ethyl]-$N^4$-(5-isopropoxy-1H-pyrazol-3-yl)pyrimidine-2,4-diamine (Example 29, 0.23 g, 0.561 mmol) was added to the suspension. The resulting mixture was stirred at 100° C. over night. It was then quenched with water and was extracted with EtOAc. The organic layer was obtained and evaporated to dryness. The dried residue was subject to silica gel chromatographic purification (by ISCO Combiflash with gradient EtOAc/hexanes) to afford the desired product as colourless oil (0.21 g, yield 74%). LC-MS: 506 (M+1).

Examples 26-28

The following compounds were prepared by the procedure similar to that of Example 25 using an appropriate starting materials.

| Ex. | Compound | LC/MS | SM |
|---|---|---|---|
| 26 | 5-Fluoro-$N^2$-[(1S)-1-(5-fluoropyridin-2-yl)ethyl]-$N^4$-(5-isopropoxy-1H-pyrazol-3-yl)-6-[(cis-2-phenyl-1,3-dioxan-5-yl)oxy]pyrimidine-2,4-diamine | 553 (M + 1) | Example 29 |
| 27 | 5-Chloro-$N^2$-[(1S)-1-(5-fluoropyridin-2-yl)ethyl]-$N^4$-(5-isopropoxy-1H-pyrazol-3-yl)-6-[(cis-2-phenyl-1,3-dioxan-5-yl)oxy]pyrimidine-2,4-diamine | LC-MS: 570 (M + 1) | Example 30 |
| 28 | 5-Chloro-6-{[(4R)-2,2-dimethyl-1,3-dioxolan-4-yl]methoxy}-$N^2$-[(1S)-1-(5-fluoropyridin-2-yl)ethyl]-$N^4$-(5-isopropoxy-1H-pyrazol-3-yl)pyrimidine-2,4-diamine | LC-MS: 522 (M + 1) | Example 30 |

Example 29

6-Chloro-5-fluoro-$N^2$-[(1S)-1-(5-fluoropyridin-2-yl)ethyl]-$N^4$-(5-isopropoxy-1H-pyrazol-3-yl)pyrimidine-2,4-diamine To a solution of 2,6-dichloro-5-fluoro-N-(5-isoproxy-1H-pyrazol-3-yl)pyrimidin-4-amine (Method 18; 0.90 g, 2.94 mmol) and (1S)-1-(5-fluoropyridin-2-yl)ethanamine (Method 6; 0.58 g, 4.12 mmol) in 1-butanol (30 ml) contained was added DIEA (0.46 g, 3.53 mmol). The reaction mixture was stirred magnetically at 100° C. overnight and then was subject to silica gel chromatographic purification (by ISCO Combiflash with gradient EtOAc/hexanes) to afford the desired product as an off-white solid (0.46 g, 38%). LC-MS, 410 (M+1); $^1$H NMR (CDCl$_3$) δ 8.35 (s, 1H), 7.64 (s, 1H), 7.35 (m, 1H), 7.20 (m, 1H), 6.25 (d, 1H), 5.62 (s, 1H), 5.30 (m, 1H), 4.70 (m, 1H), 1.50 (d, 3H), 1.30 (d, 6H).

Example 30

The following compounds were prepared by the procedure of Example 29 using the appropriate pyrimidine (the method to prepare which is also listed) and an amine.

| Ex | Compound | NMR and/or LC/MS | SM |
|---|---|---|---|
| 30 | (S)-5,6-Dichloro-N$^2$-(1-(5-fluoropyridin-2-yl)ethyl)-N$^4$-(5-isopropoxy-1H-pyrazol-3-yl)pyrimidine-2,4-diamine | $^1$H NMR (400 MHz) δ 11.96 (s, 1H), 9.86 (s, 1H), 8.53 (bs, 1H), 8.31 (d, J = 8.0 Hz, 1H), 7.68 (m, 1H), 7.46 (m, 1H), 5.56 (s, 1H), 5.05 (m, 1H), 4.68 (m, 1H), 1.46 (d, J = 6.8 Hz, 3H), 1.28 (d, J = 6.0 Hz, 6H). MS: Calcd.: 425; Found: [M + H]$^+$ 426. | Method 19 and Method 6 |

Example 31

(S)-5-Chloro-N$^4$-(5-cyclopropyl-1H-pyrazol-3-yl)-N$^2$-[1-(5-fluoro-6-methylpyridin-2-yl)ethyl]pyrimidine-2,4-diamine and Example 32

(R)-5-Chloro-N$^4$-(5-cyclopropyl-1H-pyrazol-3-yl)-N$^2$-[1-(5-fluoro-6-methylpyridin-2-yl)ethyl]pyrimidine-2,4-diamine These two enantiomers were separated from Example 5 using chiral HPLC column. The column condition were as follows:
Chiralcel OJ column, 250×20 mm, 10 μ; 80% hexane, 20% 1:1 ethanol:methanol, 0.1% diethylamine; flow rate 10 ml/min.
For the post-purification quality check:
Chiralcel OJ column, 250×4.6 mm, 10 μ
80% hexane, 20% 1:1 ethanol:methanol, 0.1% diethylamine; flow rate 0.5 ml/min
$^1$H NMR (400 MHz, CDCl$_3$) δ 0.65-0.75 (m, 2H), 0.85-0.95 (m, 2H), 1.47 (d, J=6.8 Hz, 3H), 1.82 (tt, J=8.5, 5.1 Hz, 1H), 2.46 (d, J=2.8 Hz, 3H), 4.99-5.09 (m, 1H), 6.01 (s, 1H), 6.26 (s, 1H), 7.05 (dd, J=8.3, 3.5 Hz, 1H), 7.15-7.23 (m, 1H), 7.38-7.48 (m, 1H), 7.84 (s, 1H). Calcd.: 387. Found [M+H$^+$] 388.

Example 33

5-Chloro-N$^2$-[(1S)-1-(5-fluoropyridin-2-yl)ethyl]-N$^4$-(5-isopropoxy-1H-pyrazol-3-yl)pyrimidine-2,4-diamine phosphate To a solution of 5-chloro-N$^2$-[(1S)-1-(5-fluoropyridin-2-yl)ethyl]-N$^4$-(5-isopropoxy-1H-pyrazol-3-yl)pyrimidine-2,4-diamine (Example 6; 2.46 g, 6.28 mmol) in methanol (25 ml) was added a solution of phosphoric acid (85 wt % in water, 724 mg, 6.28 mmol) in methanol (10 ml). The resulting precipitate was heated to reflux and more methanol (25 ml) was added. The precipitate was allowed to stir at reflux for 1 hour before cooling down to room temperature. The solution was filtered and filter cake obtained was washed with methanol and transferred to a round bottomed-flask for recrystallization. A suspension of the salt in methanol (50 ml) was then heated to reflux. At reflux, methanol (125 ml) was added where dissolution occurred. The excess solvent was removed by distillation to a final volume of 75 ml. The flask was removed from the heat and the solution was allowed to cool to room temperature. The resulting precipitate was filtered, washed with methanol, and vacuum dried under N$_2$ atmosphere (16 h) to afford 1.43 g (57% isolated yield) of the title compound. 1H NMR: 9.63 (s, 1H), 8.49 (s, 1H), 7.87-8.10 (m, 2H), 7.65 (t, J=8.67 Hz, 1H), 7.41 (dd, J=8.29, 4.52 Hz, 1H), 5.52 (s, 1H), 5.03 (br s, 1H), 4.65 (br s, 1H), 1.44 (d, J=6.78 Hz, 3H), 1.26 (d, J=6.03 Hz, 6H).

Example 34

5-Chloro-N$^2$-[(1S)-1-(5-fluoropyridin-2-yl)ethyl]-N$^4$-(5-methoxy-1H-pyrazol-3-yl)pyrimidine-2,4-diamine 2,5-Dichloro-N-(5-methoxy-1H-pyrazol-3-yl)pyrimidin-4-amine (Method 37; 0.25 mmol, 64 mg) and (1S)-1-(5-fluoropyridin-2-yl)ethanamine (Method 6; 0.25 mmol, 34.5 mg) were dissolved in n-BuOH (0.35 M) and DIEA (0.50 mmol, 0.08 ml) was added. The reaction was stirred at 110° C. overnight. The solvent was evaporated and the remaining material was separated between EtOAc and water, washed with brine, and dried. Evaporation of the solvent gave a brown oil (131 mg). This material was purified by Gilson (10-50% acetonitrile/H$_2$O, 15 min). The title compound was collected by evaporation of the solvent as a white solid (2.3 mg). $^1$H NMR (MeOD) 8.32 (d, 1H), 7.85-8.07 (m, 1H), 7.49 (ddd, 1H), 7.29-7.41 (m, 1H), 5.80 (s, 1H), 4.92-5.19 (m, 1H), 3.82 (s, 3H), 1.50 (d, 3H); m/z 364.

Example 35

5-Chloro-N$^2$-[(1S)-1-(5-fluoropyridin-2-yl)ethyl]-N$^4$-(5-methyl-1H-pyrazol-3-yl)pyrimidine-2,4-diamine A mixture of (S)-1-(5-fluoropyridin-2-yl)ethanamine (Method 6; 146 mg, 1.04 mmol), 2,5-dichloro-N-(5-methyl-1H-pyrazol-3-yl)pyrimidin-4-amine (Method 38; 244 mg, 1.04 mmol) and DIEA (0.39 ml) in n-BuOH (3 ml) was charged into a microwave reaction vessel. The vessel was sealed and heated in microwave reactor at 160° C. for 6 hrs. The solvent was removed under reduced pressure and the residue was purified by Gilson (10-50% acetonitrile/H$_2$O, 15 min) to give the title compound as solid (489 mg). $^1$H NMR: 12.02 (s, 1H), 8.50 (d, 1H), 7.87-7.97 (m, 114), 7.64 (ddd, 1H), 7.33-7.46 (m, 1H), 5.85 (s, 1H), 4.75-5.24 (m, 1H), 2.16-2.21 (m, 3H), 1.45 (d, 3H); m/z 349.

Example 36

N$^2$-[(1S)-1-(5-Fluoropyridin-2-yl)ethyl]-N$^4$-(5-methyl-1H-pyrazol-3-yl)-6-morpholin-4-ylpyrimidine-2,4-diamine A mixture of 6-chloro-N$^2$-[(1S)-1-(5-fluoropyridin-2-yl)ethyl]-N$^4$-(5-methyl-1H-pyrazol-3-yl)pyrimidine-2,4-diamine (Example 37; 174 mg, 0.5 mmol), morpholine (0.8 ml) and DIEA (0.13 ml) in n-BuOH (3 ml) was heated to 140° C. for 4 hrs. The solvent was removed under reduced pressure and the residue was purified by Gilson (10-50% acetonitrile/H$_2$O, 15 min) to give the title compound as solid (103 mg). $^1$H NMR: 11.09 (s, 1H), 9.21 (s, 1H), 8.36-8.66 (m, 1H), 7.74 (ddd, 1H), 7.55 (dd, 1H), 5.80-5.84 (m, 1H), 5.73 (s, 1H), 5.01-5.21 (m, 1H), 3.10-3.81 (m, 8H), 2.24 (s, 3H), 1.50 (d, 3H); m/z 399.

Example 37

6-Chloro-$N^2$-[(1S)-1-(5-fluoropyridin-2-yl)ethyl]-$N^4$-(5-methyl-1H-pyrazol-3-yl)pyrimidine-2,4-diamine To a solution of 2,5,6-trichloro-N-(5-methyl-1H-pyrazol-3-yl)pyrimidin-4-amine (Method 39; 2.0 g, 8.2 mmol) in absolute EtOH (40 ml) were added DIEA (2.5 ml) and (1S)-1-(5-fluoropyridin-2-yl)ethanamine (Method 6; 1.2 g, 8.2 mmol) and the resulting solution was heated to 140° C. for 12 hours. The mixture was partitioned between EtOAc and $H_2O$, the organic layer was washed with brine and dried. The solvents were removed under reduced pressure to give an oil which was purified by Gilson (20-75% acetonitrile/$H_2O$, 35 min) to give the titled compound as solid (762 mg). m/z: 383.

Example 38

5-Chloro-$N^2$-[1S)-1-(5-fluoropyridin-2-yl)ethyl]-$N^4$-(5-isopropoxy-1H-pyrazol-3-yl)pyrimidine-2,4-diamine maleate To a warm solution of 5-chloro-$N^2$-[(1S)-1-(5-fluoropyridin-2-yl)ethyl]-$N^4$-(5-isopropoxy-1H-pyrazol-3-yl)pyrimidine-2,4-diamine (Example 6; 1.62 g, 4.13 mmol) in 1-butanol (8.3 ml) was added maleic acid (480 mg, 4.13 mmol). The resulting solution was cooled slowly to room temperature and the salt crystallized from solution. The solution was filtered and filter cake obtained was washed with 1-butanol (1.2 ml) and vacuum dried under $N_2$ atmosphere (16 h) to afford 1.33 g (63% isolated yield) of the title compound. $^1$H NMR: 9.63 (s, 1H), 8.49 (s, 1H), 7.87-8.10 (m, 2H), 7.65 (dt, J=8.67 Hz, 1H), 7.41 (dd, J=8.29, 4.52 Hz, 1H), 6.25 (s, 2H), 5.52 (s, 1H), 5.03 (br s, 1H), 4.65 (br s, 1H), 1.44 (d, J=6.78 Hz, 3H), 1.26 (d, J=6.03 Hz, 6H).

Preparation of Starting Materials

Method 1

1-(5-Fluoropyridin-2-yl)ethanone

2-Bromo-5-fluoropyridine (13.0 g, 73.9 mmol), copper(I) iodide (2.10 g, 11.1 mmol) and dichlorobis (triphenylphosphine) palladium(II) in anhydrous acetonitrile (100 ml) was added tributyl(1-ethoxyvinyl)atannane (27.5 ml, 81.3 mmol). The reaction was heated at reflux. After heating for 70 hours, 1.5 M aqueous HCl (20 ml) was added to quench the reaction and the mixture was heated at reflux for 1 hour. After cooling to room temperature, the reaction mixture was neutralized with saturated sodium bicarbonate and extracted with ether (3×100 ml). The combined organic layers were dried over dried over sodium sulfate, and concentrated. After removal of solvent, the resulted residue was purified by column chromatography (hexane-ether=5:1) to give the title compound as a clear oil [11.3 g (75% pure), 82%]. $^1$H NMR (400 MHz, $CDCl_3$) 8.51 (d, J=3.2 Hz, 1H), 8.11 (dd, J=4.4 and 4.4 Hz, 1H), 7.51 (ddd, J=2.8, 3.2 and 2.8 Hz, 1H), 2.71 (s, 3H).

Method 2

1-(5-Fluoropyridin-2-yl)ethanol 1-(5-Fluoropyridin-2-yl)ethanone (Method 1; 11.3 g, (75% pure), 60.9 mmol) in MeOH was added sodium boronhydride (2.30 g, 60.9 mmol) potion wise at 0° C. After adding, the reaction was warmed to room temperature and stirred at room temperature for 1 hour. Water (10 ml) was added and the solution was extracted with ether (2×50 ml). The combined organic layers were dried over sodium sulfate. After removal of solvent, the resulted residue was purified by column chromatography (ether) to give the title compound as a clear oil (7.5 g, 87%). $^1$H NMR (400 MHz) 8.46 (d, J=3.2 Hz, 1H), 7.69 (ddd, J=3.2, 3.2 and 3.2 Hz, 1H), 7.55 (m, 1H), 5.44 (d, J=4.4 Hz, 1H), 4.73 (m, 1H), 1.34 (d, J=6.4 Hz, 3H).

Method 3

2-(1-Azidoethyl)-5-fluoropyridine 1-(5-Fluoropyridin-2-yl)ethanol (Method 2; 7.5 g, 53.1 mmol) and triethyl amine (9.3 ml, 66.4 mmol) in anhydrous DCM (50 ml) was added methanesulfonyl chloride (4.5 ml, 58.5 mmol) at 0° C. After adding, the reaction was warmed to room temperature and stirred at room temperature for 2 hours. The solvent was removed. The residue was dissolved in anhydrous DMF (50 ml) and sodium azide (6.9 g, 106 mmol) was added. The reaction stirred at room temperature for 2 hours. Water (50 ml) was added and extracted with ether (2×75 ml). The combined organic was dried over sodium sulfate. After removal of solvent, the resulted residue was purified by column chromatography (hexane-ether=4:1)) to give the title compound as a clear oil (7.7 g, 87%). $^1$H NMR (400 MHz) 8.60 (d, J=2.8 Hz, 1H), 7.79 (ddd, J=2.8, 2.8 and 2.8 Hz, 1H), 7.54 (m, 1H), 4.79 (q, J=6.8 Hz, 1H), 1.52 (d, J=6.8 Hz, 3H).

Method 4

1-(5-Fluoropyridin-2-yl)ethanamine 2-(1-Azidoethyl)-5-fluoropyridine (Method 3; 7.7 g, 46.3 mmol) and Pd (10 wt. %, dry basis, on activated carbon, 2.47 g, 2.32 mmol) in methanol (20 ml) was placed under $H_2$ for 4 hours. The reaction was then evacuated, flushed with $N_2$, filtered, washed with MeOH (3×30 ml), and concentrated to give the title compound as pale yellow oil (6.40 g, 99%). $^1$H NMR (400 MHz) 8.45 (d, J=2.8 Hz, 1H), 7.67 (ddd, J=2.8, 2.8 and 2.8 Hz, 1H), 7.54 (m, 1H), 4.01 (q, J=6.8 Hz, 1H), 1.97 (b, 2H), 1.27 (d, J=6.8 Hz, 3H).

Method 5

(1R,2S,5R)-2-Isopropyl-5-methylcyclohexyl[(1S)-1-(5-fluoropyridin-2-yl)ethyl]carbamate 1-(5-Fluoropyridin-2-yl)ethanamine (Method 4; 4.1 g, 24.9 mmol), (1R,2S,5R)-2-isopropyl-5-methylcyclohexyl carbonochloridate (5.3 ml, 24.9 mmol) and DIEA (4.8 ml, 27.4 mmol) in THF was stirred at room temperature for 1 hour. The solvent was removed under reduced pressure and the resulted residue was purified by column chromatography (hexane:ether=7:1) to give the title compound as white solid (3.0 g, 37%). $^1$H NMR (400 MHz, $CDCl_3$) 8.39 (d, J=2.8 Hz, 1H), 7.36 (ddd, J=3.2, 3.2 and 3.2 Hz, 1H), 7.25 (m, 1H), 5.63 (b, 1H), 4.89 (m, 1H), 4.53 (m, 1H), 2.06 (m, 1H), 1.88 (m, 1H), 1.65 (m, 2H), 1.45 (d, J=6.8 Hz, 3H), 1.30 (m, 1H), 0.95-1.06 (m, 2H), 0.85-0.91 (m, 8H), 0.72 (m, 3H). MS: Calcd.: 322. Found: [M+H]+ 323.

Method 6

(S)-1-(5-Fluoropyridin-2-yl)ethanamine (1R,2S,5R)-2-Isopropyl-5-methylcyclohexyl [(1S)-1-(5-fluoropyridin-2-ypethyl]carbamate (Method 5; 3.0 g, 9.3 mmol) and TMSI (2.7 ml, 18.6 mmol) in chloroform (10 ml) was heated at 68° C. for 24 hours. Ice water (15 ml) was added carefully and extracted with ether (2×100 ml). The aqueous layer was separated, neutralized with solid sodium bicarbonate to PH=9 and extracted with ether (5×200 ml). The combined organic was dried over sodium sulfate and concentrated to give the title compound (1.03 g, 79%) as pale yellow oil. $^1$H NMR (400 MHz) 8.44 (d, J=2.8 Hz, 1H), 7.66 (ddd, J=2.8, 2.8 and 2.8 Hz, 1H), 7.53 (m, 1H), 4.01 (q, J=6.8 Hz, 1H), 1.94 (b, 2H), 1.26 (d, J=6.8 Hz, 3H). MS: Calcd.: 140. Found: [M+H]+ 141.

Method 6 (Alternative Procedure)

(S)-1-(5-Fluoropyridin-2-yl)ethanamine

To a solution of (S)-tert-butyl-1-(5-fluoropyridin-2-yl)ethylcarbamate (Method 32; 12.8 g, 53.3 mmol) in DCM (100 ml) was added HCl/dioxane solution (107 ml, 4 N, 428 mmol). The reaction was stirred at room temperature for 3 hours. The solvent was removed and 50 ml of saturated sodium bicarbonate was added. The resulting aqueous solution was extracted with ether (6×400 ml), dried over sodium sulfate and concentrated to give the title compound (7.30 g, 98%) as pale yellow oil. $^1$H NMR (400 MHz) δ 8.44 (d, J=2.8 Hz, 1H), 7.66 (m, 1H), 7.53 (m, 1H), 4.01 (q, J=6.8 Hz, 1H), 1.94 (b, 2H), 1.26 (d, J=6.8 Hz, 3H). MS: Calcd.: 140. Found: [M+1-1]+141.

Method 7

2,5-Dichloro-4-(5-cyclopropyl-1H-pyrazole-3-ylamino)pyrimidine

A solution of 2,4,5-trichloropyrimidine (533 mg, 2.93 mmol), 3-amino-5-cyclopropyl-1H-pyrazole (360 mg, 2.93 mmol) and triethylamine (0.49 ml) in EtOH (5 ml) was stirred at room temperature for 10 hours. Solvent was removed and EtOAc was added. The solution was washed with water and dried over anhydrous sodium sulfate and was concentrated to give title compound as a white solid (546 mg, 69%). The compound was carried to the next step without further purification. $^1$H NMR δ 0.92 (m, 2H), 1.20 (m, 2H), 2.18 (m, 1H), 6.40 (s, 1H), 8.60 (s, 1H), 9.90 (s, 1H), 12.60 (s, 1H).

Methods 8-12

The following compounds were prepared by the procedure of Method 7 using the appropriate starting materials.

| Method | Compound | NMR and/or LC/MS | Pyrimidine | Amine |
|---|---|---|---|---|
| 8 | 5-Bromo-2-chloro-N-(3-cyclopropyl-1H-pyrazol-5-yl)pyrimidin-4-amine | $^1$H NMR (CDCl$_3$) δ 8.32 (s, 1H), 8.17 (s, 1H), 6.60 (s, 1H), 1.93 (m, 1H), 1.05 (m, 2H), 0.86 (m, 2H) | 5-bromo-2,4-dichloropyrimidine | 3-amino-5-cyclopropyl-1H-pyrazole |
| 9 | 2-Chloro-N-(3-cyclopropyl-1H-pyrazol-5-yl)-5-fluoropyrimidin-4-amine | $^1$H NMR (CDCl$_3$) δ 8.95 (br s, 1H), 8.07 (s, 1H), 6.61 (s, 1H), 1.91 (m, 1H), 1.05 (m, 2H), 0.84 (m, 2H) | 5-fluoro-2,4-dichloropyrimidine | 3-amino-5-cyclopropyl-1H-pyrazole |
| 10 | 2,5-Dichloro-N-(5-isopropoxy-1H-pyrazol-3-yl)pyrimidin-4-amine | LC-MS, 246 (M − 42); $^1$H NMR (CDCl$_3$) δ 8.19 (s, 1H), 7.80 (s, 1H), 5.79 (s, 1H), 4.65 (m, 1H), 1.30 (d, 6H) | 2,4,5-trichloropyrimidine | 5-isopropoxy-1H-pyrazol-3-amine |
| 11 | 2-Chloro-5-fluoro-N-(5-isoproxy-1H-pyrazol-3-yl)pyrimidin-4-amine | LC-MS, 272 (M + 1); $^1$H NMR (CDCl$_3$) δ 8.35 (br s, 1H), 8.09 (s, 1H), 5.95 (s, 1H), 4.65 (m, 1H), 1.30 (d, 6H) | 5-fluoro-2,4-dichloropyrimidine | 5-isopropoxy-1H-pyrazol-3-amine |
| 12 | 2-Chloro-5-bromo-N-(5-isopropoxy-1H-pyrazol-3-yl)pyrimidin-4-amine | $^1$H NMR (CDCl$_3$) δ 12.20 (s, 1H), 9.80 (br s, 1H), 8.45 (s, 1H), 5.85 (s, 1H), 4.60 (m, 1H), 1.30 (m, 6H) | 5-bromo-2,4-dichloropyrimidine | 5-isopropoxy-1H-pyrazol-3-amine |

Method 13

[1-(5-Fluoro-6-methylpyridin-2-yl)ethyl]amine

A 250 ml round bottom flask containing 6-(1-azidoethyl)-3-fluoro-2-methylpyridine (Method 20; 567 mg, 3.15 mmol) was charged with 10% Pd/C (242 mg) and was evacuated and backfilled with $H_2$ via a filled balloon. MeOH (6 ml) was added, and the mixture was allowed to stir at room temperature. After 1 hour, the mixture was filtered through a plug of diatomaceous earth, which was subsequently washed well with MeOH. The filtrates were concentrated to give the title compound as a pale yellow oil (404 mg, 83%). $^1$H NMR (400 MHz, CDCl$_3$) δ 1.41 (d, J=6.6 Hz, 3H), 2.05 (s, 2H), 2.50 (s, 3H), 4.14 (q, J=6.6 Hz, 1H), 7.13 (d, J=3.8 Hz, 1H), 7.28 (d, J=6.6 Hz, 1H).

Methods 14

1-(5-Fluoro-6-methylpyridin-2-yl)ethanol

A 250 ml round bottom flask containing 5-fluoro-6-methylpyridine-2-carbonitrile (Method 15; 2.24 g, 16.45 mmol) was charged with anhydrous THF (20 ml) under $N_2$. The solution was cooled to 0° C., and a solution of MeMgBr (8.5 ml of a 3.0 M solution in ether, 25.5 mmol) was added dropwise. After 1 hour at 0° C., the reaction was quenched with saturated NH$_4$Cl (10 ml, added drop wise), and the biphasic mixture was allowed to stir at 0° C. for 10 minutes. The layers were then separated, and the aqueous portion was extracted with EtOAc, and the combined organics were washed with brine, dried, filtered, and concentrated. The resulting oil was dissolved in MeOH (20 ml), and the solution was cooled to 0° C. NaBH$_4$ (634 mg, 16.8 mmol) was added in portions over 5 minutes. The reaction was allowed to stir at room temperature for 1 hour, and was then concentrated. The residue was partitioned between EtOAc and H$_2$O, and the aqueous layer was extracted with EtOAc. The combined organics were washed with brine, dried, filtered, and concentrated. The crude material was purified by silica gel chromatography (R$_f$ in 60:40 hexanes:EtOAc=0.42) to afford the title compound as a pale yellow oil (550 mg, 22% over two steps). $^1$H NMR (400 MHz, CDCl$_3$) δ 1.46 (d, J=6.6 Hz, 3H), 2.51 (d, J=3.0 Hz, 3H), 4.10 (s, 1H), 4.79-4.87 (m, 1H), 7.08 (dd, J=8.5, 3.7 Hz, 1H), 7.31 (t, J=8.7 Hz, 1H).

Methods 15

5-Fluoro-6-methylpyridine-2-carbonitrile

A 50 ml round bottom flask was charged with 2-bromo-5-fluoro-6-picoline (4.73 g, 24.89 mmol), Pd$_2$(dba)$_3$ (341 mg, 3.0 mol %), DPPF (420 mg, 3.0 mol %), zinc cyanide (1.97 g, 16.78 mmol), and zinc dust (393 mg, 6.01 mmol). The flask was evacuated and backfilled with N$_2$, and anhydrous dimethylacetamide. The mixture was allowed to stir at room temperature for 5 minutes, and was then fitted with a reflux condenser under a positive flow of N$_2$ and was placed in an oil bath preheated to 100° C. After heating overnight, the mixture was allowed to cool to room temperature and was diluted with brine (30 ml) and EtOAc (30 ml). The mixture was filtered through a pad of diatomaceous earth, which was subsequently washed well with EtOAc. The layers of the filtrate were separated, and the aqueous phase was extracted with EtOAc. The combined organics were washed with brine, dried, filtered, and concentrated. The crude oil was purified by silica gel chromatography (R$_f$ in 80:20 hexanes:EtOAc=0.39) to give the title compound as a pale yellow solid (2.24 g, 66%). $^1$H NMR (400 MHz, CDCl$_3$) δ 2.57 (d, J=3.0 Hz, 3H), 7.43 (t, J=8.69 Hz, 1H), 7.58 (dd, J=8.3, 4.3 Hz, 1H).

Method 16 tert-Butyl-1-(3,5-difluoropyridin-2-yl)ethylcarbamate

N-(1-(3,5-Difluoropyridin-2-yl)ethyl)acetamide (Method 17; 0.10 g, 0.50 mmol), DMAP (0.0122 g, 0.0999 mmol) and di-tert-butyl dicarbonate (0.218 g, 0.999 mmol) in THF (5 ml) was stirred at 50° C. for 40 hours. After cooling to room temperature, lithium hydroxide monohydrate (0.0335 g, 0.70 mmol) and water (5 ml) was added. The reaction was stirred at room temperature for 55 hours. Ether (20 ml) was added, organic layer was separated, washed with brine (10 ml) and dried over sodium sulfate. After removal of solvent, the resulted residue was purified by column chromatography (Hex-EtOAc=7:1) to give the title compound as a colourless oil (0.10 g, 77%). MS: Calcd.: 258. Found: [M+H]$^+$259.

Method 17

N-(1-(3,5-Difluoropyridin-2-yl)ethyl)acetamide

To N-(1-(3,5-difluoropyridin-2-yl)vinyl)acetamide (Method 24; 2.2 g, 11.1 mmol) in MeOH (5 ml) under N$_2$ was added 10% Pd/C (0.0537 g, 0.0505 mmol). The solution was charged with 1 atmosphere of H$_2$. The reaction was stirred at room temperature for 1 hour. The catalyst was removed by filtration and the filtrate was dried to give the title compound as a white solid (0.10 g, 99%). $^1$H NMR (400 MHz) 8.47 (d, J=2.4 Hz, 1H), 8.34 (d, J=7.2 Hz, 1H), 7.89 (m, 1H), 5.21 (m, 1H), 1.81 (s, 3H), 1.34 (d, J=6.8 Hz, 3H). MS: Calcd.: 200. Found: [M+H]$^+$ 201.

Methods 18

2,6-Dichloro-5-fluoro-N-(5-isoproxy-1H-pyrazol-3-yl)pyrimidin-4-amine

To a solution of 3-amino-5-isoproxypyrazole (1.75 g, 12.41 mmol) in THF (20 ml) was added triethylamine (1.51 g, 14.89 mmol) and then slowly a solution of 2,4,6-trichloro-5-fluoropyrimidine (WO200549033, 2.50 g, 12.41 mmol) in THF (20 ml) at 0° C. The resulting mixture was stirred at room temperature overnight. The solvent was removed in vacuo and the residue was diluted with EtOAc. The solution was then washed with brine twice. The organic layer was obtained and evaporated to dryness. The dried residue was subject to silica gel chromatographic purification (by ISCO Combiflash with gradient EtOAc/hexanes) to afford the desired product (1.40 g, yield 79%). LC-MS, 264 (M−41); $^1$H NMR (CDCl$_3$) δ 8.70 (s, 1H), 5.90 (s, 1H), 4.50 (m, 1H), 1.22 (d, 6H).

Method 19

The following compound was prepared by the procedure of Method 18 using the appropriate starting materials.

| Meth | Compound | NMR and/or LC/MS | Pyrimidine | Amine |
|---|---|---|---|---|
| 19 | 2,5,6-Trichloro-N-(5-isopropoxy-1H-pyrazol-3-yl)pyrimidin-4-amine | $^1$H NMR (400 MHz,) δ 12.25 and 11.46 (s, 1H), 10.23 and 9.94 (s, 1H), 5.85 and 5.75 (s, 1H), 4.69 and 4.45 (m, 1H), 1.30 (d, J = 6.0 Hz, 3H), 1.27 (d, J = 6.0 Hz, 3H). MS: Calcd.: 321; Found: [M + H]$^+$ 322. | 2,4,5,6-tetrachloropyrimidine | 5-isopropoxy-1H-pyrazol-3-amine |

Method 20

6-(1-Azidoethyl)-3-fluoro-2-methylpyridine

A 250 ml round bottom flask containing 1-(5-fluoro-6-methylpyridin-2-yl)ethanol (Method 14; 550 mg, 3.54 mmol) was charged with triethylamine (0.75 ml, 5.4 mmol) and anhydrous DCM (8.0 ml). The solution was cooled to 0° C., and methanesulfonyl chloride (0.32 ml, 4.1 mmol) was added dropwise. The resulting mixture was allowed to stir at room temperature for 2 hours, and the volatile components were removed using a rotary evaporator. The residue was treated with sodium azide (466 mg, 7.17 mmol) and anhydrous DMF (5.0 ml), and the slurry was allowed to stir at room temperature. After 2 hours, the mixture was partitioned between EtOAc and H$_2$O. The aqueous phase was extracted with EtOAc, and the combined organics were washed with brine, dried, filtered, and concentrated. The crude material was purified by silica gel chromatography (R$_f$ in 90:10 hexanes:EtOAc=0.47) to afford the title compound as a colourless oil (567 mg, 89%).

Method 21

(S)-1-(3,5-Difluoropyridin-2-yl)ethanamine

To a solution of (S)-tert-butyl-1-(3,5-difluoropyridin-2-yl)ethylcarbamate (Method 22; 2.05 g, 7.94 mmol) in DCM (15 ml) was added HCl/dioxane (15.9 ml, 4 N, 63.5 mmol). The reaction was stirred at room temperature for 3 hours. The solvent was removed and 10 ml of saturated sodium bicarbonate was added. The resulting aqueous solution was extracted with ether (5×100 ml), dried over sodium sulfate and concentrated to give the title compound (1.1 g, 88%) as a pale yellow oil. $^1$H NMR (400 MHz) δ 8.46 (d, J=2.0 Hz, 1H), 7.85 (m, 1H), 4.23 (q, J=6.8 Hz, 1H), 1.90 (b, 2H), 1.27 (d, J=6.8 Hz, 3H). MS: Calcd.: 158. Found: [M+H]$^+$ 159.

Method 22

(S)-tert-Butyl-1-(3,5-difluoropyridin-2-)ethylcarbamate

A solution of (S)-N-(1-(3,5-difluoropyridin-2-yl)ethyl)acetamide (Method 23; 2.0 g, 9.99 mmol), DMAP (0.244 g, 2.00 mmol), and Boc$_2$O (6.54 g, 30.0 mmol) in THF (20 ml) was stirred at 50° C. for 40 hours. After cooling to room temperature, lithium hydroxide monohydrate (0.671 g, 16.0 mmol) and water (20 ml) were added. The reaction was stirred at room temperature for 18 hours. To which was added ether (100 ml). The organic layer was separated, washed with brine (50 ml) and dried over sodium sulfate. After removal of solvent, the resulted residue was purified by column chromatography (hexane-EtOAc=5:1) to give the title compound as a colourless oil (2.05 g, 79%). $^1$H NMR (400 MHz) δ 8.45 (s, 1H), 7.87 (m, 1H), 7.24 (d, J=7.6 Hz 1H), 4.92 (m, 1H), 1.34 (s, 9H), 1.32 (d, J=7.2 Hz, 3H). MS: Calcd.: 258. Found: [M+H]$^+$ 259. Enantiomeric excess was determined by HPLC (Chiralpak ADH; 98:2 CO$_2$/MeOH), 93.6% ee.

Method 23

(S)-N-(1-(3,5-Difluoropyridin-2-yl)ethyl)acetamide

To a solution of N-(1-(3,5-difluoropyridin-2-yl)vinyl)acetamide (Method 24; 2.2 g, 11.1 mmol) in MeOH (20 ml) under N$_2$ was added (+)-1,2-bis((2S,5S)-2,5-dimethyl phospholano)benzene (cyclooctadiene)rhodium(I) trifluoromethanesulfonate (0.074 g, 0.111 mmol). The solution was transferred to a high-pressure bomb and charged 150 psi H$_2$. The reaction stirred at room temperature and maintained inside pressure between 120-150 psi for 24 hours. The solvent was removed and the resulted residue was purified by column chromatography (EtOAc) to give the title compound as a white solid (2.0 g, 90%). $^1$H NMR (400 MHz) δ 8.47 (d, J=2.4 Hz, 1H), 8.34 (d, J=7.2 Hz, 1H), 7.89 (m, 1H), 5.21 (m, 1H), 1.81 (s, 3H), 1.34 (d, J=6.8 Hz, 3H). MS: Calcd.: 200. Found: [M+H]$^+$ 201.

Method 24

N-(1-(3,5-Difluoropyridin-2-yl)vinyl)acetamide

To a mixture of (Z)-1-(3,5-difluoropyridin-2-yl)ethanone oxime (Method 25; 12.5 g, 72.6 mmol), acetic anhydride (54.8 ml, 581 mmol), and iron powder (32.4 g, 581 mmol) in DMF (100 ml) was added TMSC1 (0.01 ml, 0.073 mmol). The reaction mixture was stirred at room temperature for 18 hours, then diluted with ether (300 ml) and filtered through a short pad of celite. The filtrate was concentrated and the residue was partitioned between 200 ml of EtOAc and 50 ml of saturated sodium bicarbonate. The organic layer was separated and dried over sodium sulfate. After removal of solvent, the resulted residue was purified by column chromatography (hexane-EtOAc=2:1) to give the title compound as a white solid (2.70 g, 19%). $^1$H NMR (400 MHz) δ 9.55 (s, 1H), 8.51 (d, J=2.0 Hz, 1H), 7.97 (m, 1H), 5.87 (s, 1H), 5.14 (s, 1H), 1.99 (s, 3H). MS: Calcd.: 198. Found: [M+H]$^+$ 199.

Method 25

(Z)-1-(3,5-Difluoropyridin-2-yl)ethanone oxime

To a solution of 3,5-difluoropicolinonitrile (10.0 g, 71.4 mmol) in THF (200 ml) was added methylmagnesium bromide (61.2 ml, 85.7 mmol) in THF solution at 0° C. The reaction was stirred at room temperature for 1.5 hours. Saturated sodium bicarbonate solution (50 ml) was added, extracted with ether (100 ml), and dried over sodium sulfate. The solvent was removed. The residue (11.2 g, 71.28 mmol), hydroxylamine hydrochloride (9.907 g, 142.6 mmol) and sodium acetate (11.70 g, 142.6 mmol) in EtOH (100 ml) and water (50 ml) was heated at reflux for 3 hours. The solvent was removed and diluted with 50 ml of saturated sodium bicarbonate and extracted with EtOAc (2×200 ml). After dried over sodium sulfate, the solvent was removed and the title compound was used directly in next step without purification.

Method 26

(S)-1-(5-Bromopyridin-2-yl)ethanamine

To a solution of (S)-tert-butyl-1-(5-bromopyridin-2-yl) ethylcarbamate (Method 27; 2.0 g, 6.6 mmol) in DCM (15 ml) was added HCl/dioxane (17 ml, 4 N, 68 mmol). The reaction was stirred at room temperature for 1 hour. The solvent was removed and 10 ml of saturated sodium bicarbonate was added. The resulting aqueous solution was extracted with ether (6×100 ml), dried over sodium sulfate and concentrated to give the title compound (0.98 g, 73%) as a pale yellow oil. $^1$H NMR (400 MHz, CDCl$_3$) δ 8.60 (d, J=1.2 Hz, 1H), 7.76 (dd, J=2.0 and 8.4 Hz, 1H), 7.24 (d, J=8.0 Hz, 1H), 4.13 (q, J=6.8 Hz, 1H), 1.73 (b, 2H), 1.41 (d, J=6.4 Hz, 3H).

Method 27

(S)-tert-Butyl-1-(5-bromopyridin-2-yl)ethylcarbamate

A solution of (S)-N-(1-(5-bromopyridin-2-yl)ethyl)acetamide (Method 28; 16.0 g, 65.82 mmol), DMAP (1.61 g, 13.16 mmol), and di-tert-butyl dicarbonate (28.73 g, 131.6 mmol) in THF (100 ml) was stirred at 50° C. for 20 hours. After cooled to room temperature, lithium hydroxide monohydrate (3.31 g, 78.98 mmol) and water (100 ml) were added. The reaction was stirred at room temperature for 20 hours and then diluted with ether (200 ml). The organic layer was separated, washed with brine (100 ml), and dried over sodium sulfate. After removal of solvent, the resulted residue was purified by column chromatography (hexane-EtOAc=5:1) to give the title compound as a pale yellow oil (18.4 g, 93%). $^1$H NMR (400 MHz) δ 8.60 (d, J=2.0 Hz, 1H), 8.01 (dd, J=1.6 and 8.4 Hz, 1H), 7.40 (d, J=7.2 Hz, 1H), 7.31 (d, J=8.4 Hz, 1H), 4.62 (m, 1H), 1.37 (s, 9H), 1.31 (d, J=7.2 Hz, 3H). MS: Calcd.: 300. Found: [M+H]$^+$ 301.

Method 28

(S)-N-(1-(5-Bromopyridin-2-yl)ethyl)acetamide

To a solution of N-(1-(5-bromopyridin-2-yl)vinyl)acetamide (Method 29; 17.0 g, 70.5 mmol) in MeOH (140 ml) under N$_2$ was added (+)-1,2-bis((2S,5S)-2,5-diethylphospholano) benzene (cyclooctadiene)rhodium(I) trifluoromethanesulfonate (0.51 g, 0.705 mmol). The solution was transferred to a high pressure bomb and charged 150 psi H$_2$. The reaction stirred at room temperature and maintained inside pressure between 120-150 psi for 18 hours. The solvent was removed and the resulted residue was purified by column chromatography (EtOAc) to give the title compound as a white solid (15.8 g, 92%). $^1$H NMR (400 MHz) δ 8.62 (d, J=2.0 Hz, 1H), 8.34 (d, J=7.6 Hz, 1H), 8.00 (dd, J=2.4 and 8.4 Hz, 1H), 7.31 (d, J=8.8 Hz, 1H), 4.89 (m, 1H), 1.85 (s, 3H), 1.34 (d, J=7.2 Hz, 3H). MS: Calcd.: 242. Found: [M+H]$^+$ 243. Enantiomeric excess determined by HPLC (Chiralpak IA; 70:30 CO$_2$/MeOH), 97.9% ee.

Method 29

N-(1-(5-Bromopyridin-2-yl)vinyl)acetamide

To a solution of 2-bromo-picolinonitrile (25.8 g, 141.0 mmol) in THF (500 ml) was added a solution of MeMgBr (120.8 ml, 169.2 mmol) in THF at 0° C. The reaction was stirred at room temperature for 1.5 hours, followed by dropwise addition of acetyl chloride (15 ml, 211.5 mmol). The reaction mixture was stirred at room temperature for 16 hours. Saturated sodium bicarbonate solution (50 ml) was added and extracted with EtOAc (2×200 ml). The combined organic was dried over sodium sulfate. After removal of solvent, the resulted residue was purified by column chromatography (hexane-EtOAc=2.5:1) to give the title compound as a white solid (7.5 g, 22%). $^1$H NMR (400 MHz) δ 9.41 (s, 1H), 8.70 (d, J=2.4 Hz, 1H), 8.10 (dd, J=2.4 and 8.4 Hz, 1H), 7.73 (d, J=8.8 Hz, 1H), 6.02 (s, 1H), 5.59 (s, 1H), 2.07 (s, 3H). MS: Calcd.: 240. Found: [M+H]$^+$ 241.

Method 30

(S)-1-(5-Cyclopropylpyridin-2-yl)ethanamine hydrochloride

A solution of (S)-tert-butyl-1-(5-cyclopropylpyridin-2-yl) ethylcarbamate (Method 31; 2.04 g, 7.78 mmol) in DCM (10 ml) was treated with HCl/dioxane (9.72 ml, 4 N, 38.8 mmol) and stirred at room temperature for 2 hours. The solvent was removed to give the title compound (1.73 g, 93%) as white solid. $^1$H NMR (400 MHz) δ 8.60 (br, 3H), 8.50 (s, 1H), 7.62 (m, 1H), 7.56 (m, 1H), 4.52 (m, 1h), 2.03 (m, 1H), 1.50 (d, J=6.8 Hz, 1H), 1.04 (m, 2H), 0.79 (m, 2H). MS: Calcd.: 162. Found: [M+H]$^+$ 163.

Method 31

(S)-tert-Butyl-1-(5-cyclopropylpyridin-2-yl)ethylcarbamate

To a stirred solution of ZnBr$_2$ (7.85 g, 34.9 mmol) in THF (40 ml) was added cyclopropylmagnesium bromide (54.8 ml, 27.4 mmol) in THF dropwise at −78° C. After stirring at −78° C. for 30 minutes, the resulting solution was warmed to 0° C. and stirred at 0° C. for 30 minutes. (S)-tert-Butyl-1-(5-bromopyridin-2-yl)ethylcarbamate (Method 27; 3.00 g, 9.96 mmol) and Pd(PPh$_3$)$_4$ (0.576 g, 0.498 mmol) were added successively. The resulting mixture was stirred at 60° C. for 3 hours. After cooled to room temperature, 100 ml of saturated ammonium chloride was added, extracted with EtOAc and dried over sodium sulfate. After removal of solvent, the resulted residue was purified by column chromatography (hexane-EtOAc=4:1) to give the title compound as a white solid (2.04 g, 78%). $^1$H NMR (400 MHz) δ 8.30 (d, J=2.0 Hz, 1H), 7.37 (dd, J=1.6 and 8.0 Hz, 1H), 7.25 (d, J=7.6 Hz, 1H), 7.20 (d, J=8.4 Hz, 1H), 4.61 (m, 1H), 1.92 (m, 1H), 1.37 (s, 9H), 1.29 (d, J=7.2 Hz, 3H), 0.96 (m, 2H), 0.69 (m, 2H). MS: Calcd.: 262. Found: [M+H]$^+$263.

Method 32

(S)-tert-Butyl-1-(5-fluoropyridin-2-yl)ethylcarbamate

A solution of (S)-N-(1-(5-fluoropyridin-2-yl)ethyl)acetamide (Method 33; 11.0 g, 60.37 mmol), DMAP (1.48 g, 12.07 mmol) and Boc$_2$O (26.35 g, 120.7 mmol) in THF (100 ml) was stirred at 50° C. for 20 hours. After cooled to room temperature, lithium hydroxide monohydrate (5.19 g, 123.8 mmol) and water (100 ml) were added. The reaction was stirred at rt for 5 hrs and diluted with ether (200 ml). The organic layer was separated, washed with brine (100 ml), and dried over sodium sulfate. After removal of solvent, the resulted residue was purified by column chromatography (Hexane-EtOAc=5:1) to give the title compound as a pale yellow oil (13.6 g, 94%). $^1$H NMR (400 MHz) δ 8.46 (d, J=2.8 Hz, 1H), 7.69 (m, 1H), 7.35-7.41 (m, 2H), 4.67 (m, 1H), 1.37 (s, 9H), 1.32 (d, J=7.2 Hz, 3H). MS: Calcd.: 240. Found: [M+H]$^+$241.

Method 33

(S)-N-(1-(5-Fluoropyridin-2-yl)ethyl)acetamide

To a solution of N-(1-(5-fluoropyridin-2-yl)vinyl)acetamide (Method 34; 11.0 g, 61.1 mmol) in MeOH (120 ml) under N$_2$ was added (+)-1,2-bis((2S,5S)-2,5-diethylphospholano)benzene (cyclooctadiene)rhodium(I) trifluoromethanesulfonate (0.441 g, 0.611 mmol). The solution was transferred to a high pressure bomb and charged 150 psi H$_2$. The reaction stirred at room temperature and maintained inside pressure between 120-150 psi for 7 hours. The solvent was removed and the resulted residue was purified by column chromatography (EtOAc) to give the title compound as a white solid (9.8 g, 88%). $^1$H NMR (400 MHz) δ 8.49 (d, J=2.4 Hz, 1H), 8.32 (d, J=7.6 Hz, 1H), 7.66 (m, 1H), 7.39 (dd, J=4.4 and 8.8 Hz, 1H), 4.95 (m, 1H), 1.85 (s, 3H), 1.34 (d, J=7.2 Hz, 3H). MS: Calcd.: 182. Found: [M+H]$^+$ 183. Enantiomeric excess determined by HPLC (Chiralpak IA; 70:30 CO$_2$/MeOH), 95.3% ee.

Method 33 (Alternative Procedure)

(S)-N-(1-(5-Fluoropyridin-2-yl)ethyl)acetamide

To a solution of N-(1-(5-fluoropyridin-2-yl)vinyl)acetamide (Method 34; 99.7 g, 0.55 mol) in MeOH (1 l) under N$_2$ was added (1,2bis((2S,5S)-2,5-diethylphospholano)benzene (1,5-cyclooctadiene)rhodium (1) tetrafluoroborate (4 g, 6.11 mmol). The solution was hydrogenated at 5 BAR, 25° for 18 hours. The mixture was concentrated to dryness to give a dark brown oil which was purified by chromatography (60% EtOAc/isohexane, Merck Lichroprep). The isolated solid was dried in a vacuum oven at 45° C. to give a solid 86 g, 86% theory containing <1% of the unwanted enantiomer.

Method 34

N-(1-(5-Fluoropyridin-2-yl)vinyl)acetamide

A solution of MeMgBr (170.3 ml, 510.98 mmol) in ether was diluted with 170 ml of anhydrous THF and cooled to 0° C. 5-Fluoropicolinontrile (Method 35; 53.6 g, 425.82 mmol) in THF (170 ml) was added dropwise. The reaction was stirred at 0° C. for 30 minutes, then diluted with DCM (170 ml). Acetic anhydride (48.3 ml, 510.98 mmol) in DCM (100 ml) was added dropwise at 0° C. After addition, the reaction was warmed to room temperature and stirred at room temperature for 8 hrs. Saturated sodium bicarbonate solution (50 ml) was added and extracted with EtOAc (2×200 ml). The combined organic was dried over sodium sulfate. After removal of solvent, the resulted residue was purified by column chromatography (hexane-EtOAc=2.5:1) to give the title compound as a white solid (26.6 g, 35%). $^1$H NMR (400 MHz) δ 9.37 (s, 1H), 8.57 (d, J=2.8 Hz, 1H), 7.81 (m, 2H), 6.01 (s, 1H), 5.52 (s, 1H), 2.08 (s, 3H). MS: Calcd.: 180. Found: [M+H]$^+$ 181.

Method 34 (Alternative Procedure)

N-(1-(5-Fluoropyridin-2-yl)vinyl)acetamide

A solution of 5-fluoropicolinonitrile (Method 35; 1875 g 1 equivalent) in THF (3.7 volumes) was added to methyl magnesium chloride (3N in THF, 1.2 equivalents) maintaining the temperature at 0° C. The reaction mixture was stirred for 30 minutes at 0° C. and then diluted with DCM (3.2 volumes) at 0° C. Acetic anhydride (2.0 equivalents) in DCM (1.6 volumes.) was added at a rate to maintain the temperature at 0° C. The batch was allowed to warm to room temperature and stirred overnight. Saturated, aqueous sodium hydrogen carbonate (13.9 volumes) was added and the product was extracted into EtOAc (1×0.53 volumes, 1×0.26 volumes). The combined extracts were dried, filtered and evaporated in vacuo and purification carried out by chromatography (5 w/w silica; 20-100% DCM in hexane). The mixture of N-mono and N,N-di-acetylated compounds was treated with potassium carbonate (0.1 w/w on mixture) in methanol (5 volumes) for 30 minutes. The inorganic solids were filtered and washed with methanol. Silica was added to the methanol solution to remove residual potassium carbonate prior to evaporation. The product, pre-adsorbed on silica, was eluted through a silica pad (2 w/w silica; 90-100% DCM in hexane) and evaporated to give an orange solid. Mp 61.0-62.2° C., 636 g, 23.0% theory.

Method 35

5-Fluoropicolinontrile

2-Bromo-5-fluoropyridine (93.0 g, 528 mmol), Zn dust (8.29 g, 127 mmol), zinc cyanide (40.3 g, 343 mmol), 1,1'-bis(diphenylphosphino)ferrocene (11.7 g, 21.1 mmol) and Pd$_2$ dba$_3$ (9.68 g, 10.6 mmol) in anhydrous DMA (300 ml) was heated at 95° C. for 3 hours. After cooled to room temperature, brine (100 ml) and ether (500 ml) was added. The solid formed was removed by filtration and washed with ether (300 ml). The organic layer was separated, washed with brine (200 ml) and dried over sodium sulfate, and concentrated. After removal of solvent, the resulted residue was purified by column chromatography (hexane-DCM°1:1) to give the title compound as a white solid (49 g, 72%). $^1$H NMR (400 MHz) δ 8.82 (d, J=2.8 Hz, 1H), 8.21 (dd, J=4.4 and 8.8 Hz, 1H), 8.05 (dd, J=2.8 and 8.8 Hz, 1H).

Method 35 (alternative procedure)

5-Fluoropicolinonitrile

2-Bromo-5-fluoropyridine (recrystallized from 0.3 volumes of pentane, 1240 g, 1 equivalent) was dissolved in dimethylacetamide (2 volumes), the mixture was heated to 60-70° C. and cuprous cyanide (0.4 equivalents) was added in one portion, giving a dark green solution. Heating was continued and potassium cyanide (1.2 equivalents) was added in portions above 90° C. After completion of the addition, the resulting brown suspension was heated to 145° C. for 5 hours. The reaction mixture was allowed to cool to room temperature and poured into cold water (14 volumes). Ethylene diamine (1.2 equivalents) was added and the solution extracted with methyl t-butyl ether (4×5 volumes). The combined extracts were dried filtered and evaporated in vacuo with a bath temperature no higher than 45° C. The crude solid was purified by silica pad chromatography (5 w/w silica; 10-33% methyl t-butyl ether in 40/60 petroleum ether). Product containing fractions were evaporated to give a white crystalline solid. Mp 40-41° C., 541 g, 62.9% theory.

Method 36

1-(3,5-Difluoropyridin-2-yl)ethanamine

To tert-butyl-1-(3,5-difluoropyridin-2-yl)ethylcarbamate (Method 16; 0.10 g, 0.39 mmol) in DCM (2 ml) was added HCl (0.8 ml, 3.12 mmol) in dioxane. The reaction was stirred at room temperature for 3 hours. The solvent was removed and 10 ml of saturated sodium bicarbonate was added. The resulting aqueous solution was extracted with ether (5×30 ml), dried over sodium sulfate and concentrated to give the title compound (0.06 g, 95%) as pale yellow oil. MS: Calcd.: 158. Found: $[M+H]^+$ 159.

Method 37

2,5-Dichloro-N-(5-methoxy-1H-pyrazol-3-yl)pyrimidin-4-amine

To a solution of 5-methoxy-1H-pyrazol-3-amine (890 mg, 7.8 mmol) in absolute EtOH (20 ml) were added triethylamine (3.3 ml, 23.6 mmol), 2,4,5-trichloropyrimidine (1.4 g, 7.8 mmol) and the resulting solution was aged at room temperature for 12 hours. The mixture was partitioned between EtOAc and $H_2O$, the organic layer was washed with brine and dried. The solvents were removed under reduced pressure to give the title compound as an oil which crystallized upon standing (1.8 g). m/z: 261.

Methods 38-39

The following compounds were prepared by the procedure of Method 37 using the appropriate starting material.

| Meth | Compound | m/z | SM |
| --- | --- | --- | --- |
| 38 | 2,5-Dichloro-N-(5-methyl-1H-pyrazol-3-yl)pyrimidin-4-amine | 245 | 5-methyl-1H-pyrazol-3-amine and 2,4,5-trichloropyrimidine |
| 39 | 2,5,6-Trichloro-N-(5-methyl-1H-pyrazol-3-yl)pyrimidin-4-amine | 279 | 5-methyl-1H-pyrazol-3-amine and 2,4,5,6-tetrachloropyrimidine |

Utility

The compounds of the present invention have utility for the treatment of cancer by inhibiting the tyrosine kinases, particularly the Trks and more particularly Trk A and B. Methods of treatment target tyrosine kinase activity, particularly the Trk activity and more particularly Trk A and B activity, which is involved in a variety of cancer related processes. Thus, inhibitors of tyrosine kinase, particularly the Trks and more particularly Trk A and B, are expected to be active against neoplastic disease such as carcinoma of the breast, ovary, lung, colon, prostate or other tissues, as well as leukemias and lymphomas, tumours of the central and peripheral nervous system, and other tumour types such as melanoma, fibrosarcoma and osteosarcoma. Tyrosine kinase inhibitors, particularly the Trk inhibitors and more particularly Trk A and B inhibitors are also expected to be useful for the treatment other proliferative diseases including but not limited to autoimmune, inflammatory, neurological, and cardiovascular diseases.

In addition, the compounds of the invention are expected to be of value in the treatment or prophylaxis of cancers selected with up regulated of constitutively activated Trk kinases, including but not limited to, oncogenic rearrangements leading to ETV6-TrkC fusions, TRP-TrkA fusions proteins, AML-ETO (t8; 21), autocrine or paracrine signalling leading to elevated serum levels of NGF, BDNF, neurotropins or tumours with constitutively active Trk associated with disease aggressiveness, tumour growth and proliferation or survival signalling.

Compounds of the present invention have been shown to inhibit tyrosine kinases, particularly the Trks and more particularly Trk A and B, as determined by the Trk A Assay described herein.

Compounds provided by this invention should also be useful as standards and reagents in determining the ability of a potential pharmaceutical to inhibit tyrosine kinases, particularly the Trks and more particularly Trk A and B. These would be provided in commercial kits comprising a compound of this invention Trk A Assay Format Trk A kinase activity was measured for its ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure Trk A kinase activity, the intracellular domain of a HIS-tagged human Trk A kinase (amino acids 442-796 of Trk A, Swiss-Prot Primary Accession Number $PO_{4629}$) was expressed in SF9 cells and purified using standard nickel column chromatography. After incubation of the kinase with a biotinylated substrate and adenosine triphosphate (ATP) for 20 minutes at room temperature, the kinase reaction was stopped by the addition of 30 mM ethylenediaminetetraacetic acid (EDTA). The reaction was performed in 384 well microtitre plates and the reaction products were detected with the addition of strepavidin coated Donor Beads and phosphotyrosine-specific antibodies coated Acceptor Beads using the EnVision Multilabel Plate Reader after an overnight incubation at room temperature.

| | |
|---|---|
| Peptide substrate | PolyEY-biotin (PGT-bio.) |
| ATP Km | 70 μM |
| Assay conditions | 0.838 ng/ml Trk A, 9 mM HEPES, 45 μg/ml BSA, 10 mM $MnCl_2$, 5 nM PGT-bio, 0.01% Triton ® X-100, 70 μM ATP |
| Incubation | 20 minutes, room temperature |
| Termination/Detection conditions | 6.3 mM HEPES, 30 mM EDTA, 525 μg/ml BSA, 40 mM NaCl, 0.007% Triton ® X-100, 12 ng/ml of Donor Beads, 12 ng/ml of Acceptor Beads |
| Detection incubation | overnight, room temperature |
| Fluometer settings | Excitation = 680 nM Emission = 570 nM Excitation Time = 180 ms Total Measurement Time = 550 ms |

Although the pharmacological properties of the compounds of the formula (I) vary with structural change, in general activity possessed by compounds of the formula (I) may be demonstrated at $IC_{50}$ concentrations (concentrations to achieve 50% inhibition) or doses in the range of (0.01 μM to 10 μM).

When tested in the above in-vitro assay the Trk inhibitory activity of the following examples was measured at the following $IC_{50}$s.

| Ex | $IC_{50}$ (μM) |
|---|---|
| 1 | 0.005 |
| 2 | 0.008 |
| 3 | 0.010 |

The invention claimed is:

1. A compound which is:
(S)-5-Bromo-$N^4$-(5-cyclopropyl-1H-pyrazol-3-yl)-$N^2$-(1-(5-fluoropyridin-2-yl)ethyl)pyrimidine-2,4-diamine;
(S)-5-Chloro-$N^4$-(5-cyclopropyl-1H-pyrazol-3-yl)-$N^2$-(1-(5-fluoropyridin-2-yl)ethyl)pyrimidine-2,4-diamine;
(S)-5-Fluoro-$N^4$-(5-cyclopropyl-1H-pyrazol-3-yl)-$N^2$-(1-(5-fluoropyridin-2-yl)ethyl)pyrimidine-2,4-diamine;
5-Chloro-$N^4$-(5-cyclopropyl-1H-pyrazol-3-yl)-$N^2$-(1-(5-fluoropyridin-2-yl)ethyl)pyrimidine-2,4-diamine;
5-Chloro-$N^4$-(5-cyclopropyl-1H-pyrazol-3-yl)-$N^2$-[1-(5-fluoro-6-methylpyridin-2-yl)ethyl]pyrimidine-2,4-diamine;
5-Chloro-$N^2$-[(1S)-1-(5-fluoropyridin-2-yl)ethyl]-$N^4$-(5-isopropoxy-1H-pyrazol-3-yl)pyrimidine-2,4-diamine;
5-Fluoro-$N^2$-[(1S)-1-(5-fluoropyridin-2-yl)ethyl]-1$N^4$-(5-isopropoxy-1H-pyrazol-3-yl)pyrimidine-2,4-diamine;
(S)-5-Bromo-$N^2$-(1-(5-fluoropyridin-2-yl)ethyl)-$N^4$-(5-isopropoxy-1H-pyrazol-3-yl)pyrimidine-2,4-diamine;
(S)-2-(5-Chloro-2-(1-(5-fluoropyridin-2-yl)ethylamino)-6-(5-isopropoxy-1H-pyrazol-3-ylamino)pyrimidin-4-ylamino)propane-1,3-diol;
(R)-3-(5-Chloro-2-((S)-1-(5-fluoropyridin-2-yl)ethylamino)-6-(5-isopropoxy-1H-pyrazol-3-ylamino)pyrimidin-4-ylamino)propane-1,2-diol;
(2S)-3-({5-Fluoro-2-{[(1S)-1-(5-fluoropyridin-2-yl)ethyl]amino}-6-[(5-isopropoxy-1H-pyrazol-3-yl)amino]pyrimidin-4-yl}oxy)propane-1,2-diol;
2-({5-Fluoro-2-{[(1S)-1-(5-fluoropyridin-2-yl)ethyl]amino}-6-[(5-isopropoxy-1H-pyrazol-3-yl)amino]pyrimidin-4-yl}oxy)propane-1,3-diol;
(S)-2-(5-Chloro-2-(1-(5-fluoropyridin-2-yl)ethylamino)-6-(5-isopropoxy-1H-pyrazol-3-ylamino)pyrimidin-4-yloxy)propane-1,3-diol;
(S)-2-(2-(1-(5-Fluoropyridin-2-yl)ethylamino)-6-(5-isopropoxy-1H-pyrazol-3-ylamino) pyrimidin-4-yloxy)propane-1,3-diol;
(S)-3-(5-Chloro-2-((S)-1-(5-fluoropyridin-2-yl)ethylamino)-6-(5-isopropoxy-1H-pyrazol-3-ylamino)pyrimidin-4-yloxy)propane-1,2-diol;
(S)-5-Chloro-$N^2$-(1-(5-fluoropyridin-2-yl)ethyl)-$N^4$-(5-isopropoxy-1H-pyrazol-3-yl)pyrimidine-2,4,6-triamine;
(S)-5-Chloro-$N^4$-(5-cyclopropyl-1H-pyrazol-3-yl)-$N^2$-(1-(3,5-difluoropyridin-2-yl)ethyl)pyrimidine-2,4-diamine;
(S)-5-Chloro-$N^2$-(1-(3,5-difluoropyridin-2-yl)ethyl)-$N^4$-(5-isopropoxy-1H-pyrazol-3-yl)pyrimidine-2,4-diamine;
(S)-5-Bromo-$N^2$-(1-(3,5-difluoropyridin-2-yl)ethyl)-$N^4$-(5-isopropoxy-1H-pyrazol-3-yl)pyrimidine-2,4-diamine;
(S)-$N^2$-(1-(3,5-Difluoropyridin-2-yl)ethyl)-5-fluoro-$N^4$-(5-isopropoxy-1H-pyrazol-3-yl)pyrimidine-2,4-diamine;
5-Chloro-$N^4$-(5-cyclopropyl-1H-pyrazol-3-yl)-$N^2$-(1-(3,5-difluoropyridin-2-yl)ethyl)pyrimidine-2,4-diamine;
(S)-$N^2$-(1-(5-Bromopyridin-2-yl)ethyl)-5-chloro-$N^4$-(5-cyclopropyl-1H-pyrazol-3-yl)-pyrimidine-2,4-diamine;
(S)-$N^2$-(1-(5-Bromopyridin-2-yl)ethyl)-$N^4$-(5-cyclopropyl-1H-pyrazol-3-yl)-5-fluoropyrimidine-2,4-diamine;
(S)-$N^4$-(5-Cyclopropyl-1H-pyrazol-3-yl)-5-chloro-$N^2$-(1-(5-cyclopropylpyridin-2-yl)ethyl)-pyrimidine-2,4-diamine;
6-{[(4R)-2,2-Dimethyl-1,3-dioxolan-4-yl]methoxy}-5-fluoro-$N^2$[(1S)-1-(5-fluoropyridin-2-yl)ethyl]-$N^4$-(5-isopropoxy-1H-pyrazol-3-yl)pyrimidine-2,4-diamine;
5-Fluoro-$N^2$-[(1S)-1-(5-fluoropyridin-2-yl)ethyl]-$N^4$-(5-isopropoxy-1H-pyrazol-3-yl)-6-[(cis-2-phenyl-1,3-dioxan-5-yl)oxy]pyrimidine-2,4-diamine;
5-Chloro-$N^2$-[(1S)-1-(5-fluoropyridin-2-yl)ethyl]-$N^4$-(5-isopropoxy-1H-pyrazol-3-yl) -6-[(cis-2-phenyl-1,3-dioxan-5-yl)oxy]pyrimidine-2,4-diamine;
5-Chloro-6-{[(4R)-2,2-dim1ethyl-1,3-dioxolan-4-yl]methoxy}-$N^2$-[(1S)-1-(5-fluoropyridin-2-yl)ethyl]-$N^4$-(5-isopropoxy-1H-pyrazol-3-yl)pyrimidine-2,4-diamine;
6-Chloro-5-fluoro-$N^2$-[(1S)-1-(5-fluoropyridin-2-yl)ethyl]-$N^4$-(5-isopropoxy-1H-pyrazol-3-yl)pyrimidine-2,4-diamine;
(S)-5,6-Dichloro-$N^2$-(1-(5-fluoropyridin-2-yl)ethyl)-$N^4$-(5-isopropoxy-1H-pyrazol-3-yl)pyrimidine-2,4-diamine;
(S)-5-Chloro-$N^4$-(5-cyclopropyl-1H-pyrazol-3-yl)-$N^2$-[1-(5-fluoro-6-methylpyridin-2-yl)ethyl]pyrimidine-2,4-diamine;

(R)-5-Chloro-$N^4$-(5-cyclopropyl-1H-pyrazol-3-yl)-$N^2$-[1-(5-fluoro-6-methylpyridin-2-yl)ethyl]pyrimidine-2,4-diamine;

5-Chloro-$N^2$-[(1S)-1-(5-fluoropyridin-2-yl)ethyl]-$N^4$-(5-isopropoxy-1H-pyrazol-3-yl)pyrimidine-2,4-diamine phosphate;

5-Chloro-$N^2$-[(1S)-1-(5-fluoropyridin-2-yl)ethyl]-$N^4$-(5-methoxy-1H-pyrazol-3-yl)pyrimidine-2,4-diamine;

5-Chloro-$N^2$-[(1S)-1-(5-fluoropyridin-2-yl)ethyl]-$N^4$-(5-methyl-1H-pyrazol-3-yl)pyrimidine-2,4-diamine;

$N^2$-[(1S)-1-(5-Fluoropyridin-2-yl)ethyl]-$N^4$-(5-methyl-1H-pyrazol-3-yl)-6-morpholin-4-ylpyrimidine-2,4-diamine;

6-Chloro-$N^2$-[(1S)-1-(5-fluoropyridin-2-yl)ethyl]-$N^4$-(5-methyl-1H-pyrazol-3-yl)pyrimidine-2,4-diamine; or 5-Chloro-$N^2$-[(1S)-1-(5-fluoropyridin-2-yl)ethyl]-$N^4$-(5-isopropoxy-1H-pyrazol-3-yl)pyrimidine-2,4-diamine; or a pharmaceutically acceptable salt thereof

* * * * *